United States Patent
Lenehan et al.

(10) Patent No.: US 10,568,582 B2
(45) Date of Patent: Feb. 25, 2020

(54) SYSTEM AND METHOD FOR USING FLOW-MEDIATED DILATION TO PROVIDE AN ADJUSTED VASCULAR AGE AS AN INDICATOR OF RISK OF CARDIOVASCULAR DISEASE

(71) Applicant: Everist Genomics, Inc., Ann Arbor, MI (US)

(72) Inventors: Peter F. Lenehan, Chelsea, MI (US); Thomas Stephen Everist, III, Denver, CO (US)

(73) Assignee: Everist Genomics, Inc., Ann Arbor, MI (US)

( * ) Notice: Subject to any disclaimer, the term of this patent is extended or adjusted under 35 U.S.C. 154(b) by 122 days.

(21) Appl. No.: 14/774,632

(22) PCT Filed: Mar. 13, 2014

(86) PCT No.: PCT/US2014/026895
§ 371 (c)(1),
(2) Date: Sep. 10, 2015

(87) PCT Pub. No.: WO2014/160515
PCT Pub. Date: Oct. 2, 2014

(65) Prior Publication Data
US 2016/0029972 A1 Feb. 4, 2016

Related U.S. Application Data

(60) Provisional application No. 61/778,424, filed on Mar. 13, 2013.

(51) Int. Cl.
*A61B 5/00* (2006.01)
*A61B 5/02* (2006.01)
(Continued)

(52) U.S. Cl.
CPC ........ *A61B 5/7275* (2013.01); *A61B 5/02007* (2013.01); *A61B 5/02055* (2013.01);
(Continued)

(58) Field of Classification Search
CPC . A61B 5/7275; A61B 5/6898; A61B 5/02116; A61B 5/0295; A61B 5/4806; A61B 5/02108
See application file for complete search history.

(56) References Cited

U.S. PATENT DOCUMENTS

2008/0119743 A1* 5/2008 Friedman ........... A61B 5/02007
600/490
2009/0276161 A1* 11/2009 Cobain ............... G06F 19/3431
702/19
(Continued)

FOREIGN PATENT DOCUMENTS

WO 2012/116997 A1 9/2012

OTHER PUBLICATIONS

D'Agostino, Sr., RB, et al.; General Cardiovascular Risk Profile for Use in Primary Care. The Framingham heart study. Circulation. 2008. vol. 117. pp. 743-753.
(Continued)

*Primary Examiner* — Lynsey C Eiseman
*Assistant Examiner* — Amanda L Steinberg
(74) *Attorney, Agent, or Firm* — Dykema Gossett PLC

(57) ABSTRACT

A diagnostic tool 104 and method 300 are used to modify vascular age scoring systems using flow-mediated dilation (FMD) data. The resulting FMD-adjusted vascular age calculator can be used to diagnose a person's potential for developing cardiovascular disease.

22 Claims, 15 Drawing Sheets

(51) Int. Cl.
*A61B 5/0205* (2006.01)
*A61B 5/0295* (2006.01)
*A61B 5/026* (2006.01)
*A61B 8/06* (2006.01)

(52) U.S. Cl.
CPC .......... *A61B 5/0295* (2013.01); *A61B 5/4806* (2013.01); *A61B 5/6898* (2013.01); *A61B 5/7278* (2013.01); *A61B 5/742* (2013.01); *A61B 5/0022* (2013.01); *A61B 5/0261* (2013.01); *A61B 8/06* (2013.01); *A61B 2560/0475* (2013.01)

(56) References Cited

U.S. PATENT DOCUMENTS

| | | |
|---|---|---|
| 2011/0270051 A1 | 11/2011 | Naghavi et al. |
| 2014/0128747 A1* | 5/2014 | Maltz ................ A61B 5/02007 600/481 |

OTHER PUBLICATIONS

Inaba, Y., et al.; Prediction of future cardiovascular outcomes by flow-mediated vasodilatation of brachial artery: a meta-analysis. The International Journal of Cardiovascular Imaging. 2010. vol. 26. pp. 631-640.

Stein, JH, et al. Vascular Age: Integrating Carotid Intima-Media Thickness Measurements with Global Coronary Risk Assessment; Clinical Clinical Cardiology. 2004. vol. 27. pp. 388-392.

Cuende, JI, et al. How to calculate vascular age with Score project scales: a new method of cardiovascular risk evaluation. European Heart Journal. 2010. vol. 31. pp. 2351-2358.

Bots, ML, et al. Assessment of flow-mediated vasodilatation (FMD) of the brachial artery: effects of technical aspects of the FMD measurement on the FMD response. European Heart Journal. 2005. vol. 26. pp. 363-368.

\* cited by examiner

EXTRAPOLATED FRAMINGHAM CVD RISK SCORES (%) -- MEN/NO LABS

| Framingham Total Points Factor x FMD 10 Score: | 0 | 1 | 2 | 3 | 4 | 5 | 6 | 7 | 8 | 9 | 10 | 11 | 12 | 13 | 14 | 15+ |
|---|---|---|---|---|---|---|---|---|---|---|---|---|---|---|---|---|
| -9 | 4.03 | 3.50 | 3.05 | 2.65 | 2.31 | 2.01 | 1.75 | 1.52 | 1.32 | 1.15 | 1.00 | 0.87 | 0.76 | 0.66 | 0.57 | 0.50 |
| -8 | 1.93 | 1.68 | 1.16 | 1.27 | 1.11 | 0.10 | 0.84 | 0.73 | 0.63 | 0.55 | 0.48 | 0.42 | 0.36 | 0.32 | 0.27 | 0.24 |
| -7 | 2.33 | 2.03 | 1.77 | 1.54 | 1.34 | 1.16 | 1.01 | 0.88 | 0.77 | 0.67 | 0.58 | 0.50 | 0.44 | 0.38 | 0.33 | 0.29 |
| -6 | 2.74 | 2.38 | 2.07 | 1.80 | 1.57 | 1.36 | 1.19 | 1.03 | 0.90 | 0.78 | 0.68 | 0.59 | 0.51 | 0.45 | 0.39 | 0.34 |
| -5 | 3.26 | 2.84 | 2.47 | 2.15 | 1.87 | 1.63 | 1.41 | 1.23 | 1.07 | 0.93 | 0.81 | 0.70 | 0.61 | 0.53 | 0.46 | 0.40 |
| -4 | 3.91 | 3.40 | 2.96 | 2.57 | 2.24 | 1.95 | 1.69 | 1.47 | 1.28 | 1.11 | 0.97 | 0.84 | 0.73 | 0.64 | 0.56 | 0.48 |
| -3 | 4.43 | 3.85 | 3.35 | 2.92 | 2.54 | 2.21 | 1.92 | 1.67 | 1.45 | 1.26 | 1.10 | 0.96 | 0.83 | 0.72 | 0.63 | 0.55 |
| -2 | 5.63 | 4.90 | 4.27 | 3.71 | 3.23 | 2.81 | 2.44 | 2.13 | 1.85 | 1.61 | 1.40 | 1.23 | 1.06 | 0.92 | 0.80 | 0.70 |
| -1 | 6.44 | 5.60 | 4.87 | 4.24 | 3.69 | 3.21 | 2.79 | 2.43 | 2.11 | 1.84 | 1.60 | 1.39 | 1.21 | 1.05 | 0.92 | 0.80 |
| 0 | 7.64 | 6.65 | 5.79 | 5.04 | 4.38 | 3.81 | 3.32 | 2.89 | 2.51 | 2.18 | 1.90 | 1.65 | 1.44 | 1.25 | 1.09 | 0.95 |
| 1 | 9.25 | 8.05 | 7.01 | 6.10 | 5.30 | 4.61 | 4.01 | 3.49 | 3.04 | 2.64 | 2.30 | 2.00 | 1.74 | 1.51 | 1.32 | 1.15 |
| 2 | 11.28 | 9.81 | 8.53 | 7.42 | 6.46 | 5.62 | 4.89 | 4.25 | 3.70 | 3.22 | 2.80 | 2.44 | 2.12 | 1.84 | 1.60 | 1.40 |
| 3 | 13.29 | 11.56 | 10.05 | 8.75 | 7.61 | 6.62 | 5.76 | 5.01 | 4.36 | 3.79 | 3.30 | 2.87 | 2.50 | 2.17 | 1.89 | 1.64 |
| 4 | 16.10 | 14.01 | 12.19 | 10.60 | 9.22 | 8.03 | 6.98 | 6.07 | 5.28 | 4.60 | 4.00 | 3.48 | 3.03 | 2.63 | 2.29 | 1.99 |
| 5 | 18.92 | 16.46 | 14.32 | 12.46 | 10.84 | 9.43 | 8.20 | 7.14 | 6.21 | 5.40 | 4.70 | 4.09 | 3.56 | 3.09 | 2.69 | 2.34 |
| 6 | 22.54 | 19.61 | 17.06 | 14.84 | 12.91 | 11.24 | 9.77 | 8.50 | 7.40 | 6.44 | 5.60 | 4.87 | 4.24 | 3.69 | 3.21 | 2.79 |
| 7 | 27.01 | 23.50 | 20.41 | 17.76 | 15.45 | 13.44 | 11.69 | 10.17 | 8.85 | 7.70 | 6.70 | 5.83 | 5.07 | 4.41 | 3.84 | 3.34 |
| 8 | 32.18 | 28.00 | 24.40 | 21.20 | 18.40 | 16.10 | 14.00 | 12.10 | 10.60 | 9.20 | 8.00 | 6.96 | 6.06 | 5.27 | 4.58 | 3.99 |
| 9 | | 33.30 | 28.90 | 25.20 | 21.90 | 19.10 | 16.60 | 14.40 | 12.60 | 10.90 | 9.50 | 8.27 | 7.19 | 6.26 | 5.44 | 4.73 |
| 10 | | | 34.10 | 29.70 | 25.80 | 22.50 | 19.50 | 17.00 | 14.80 | 12.90 | 11.20 | 9.74 | 8.48 | 7.38 | 6.42 | 5.58 |
| 11 | | | | | 30.70 | 26.70 | 23.20 | 20.20 | 17.60 | 15.30 | 13.00 | 11.57 | 10.07 | 8.76 | 7.62 | 6.63 |
| 12 | | | | | | 31.50 | 27.40 | 23.80 | 20.70 | 18.00 | 15.70 | 13.66 | 11.88 | 10.34 | 8.99 | 7.83 |
| 13 | | | | | | | 32.30 | 28.10 | 24.40 | 21.30 | 18.50 | 16.10 | 14.00 | 12.18 | 10.60 | 9.22 |
| 14 | | | | | | | | 33.00 | 28.70 | 24.90 | 21.70 | 18.88 | 16.42 | 14.29 | 12.43 | 10.82 |
| 15 | | | | | | | | | 33.60 | 29.20 | 25.40 | 22.10 | 19.22 | 16.73 | 14.55 | 12.66 |
| 16+ | | | | | | | | | | 34.00 | 29.60 | 25.80 | 22.40 | 19.50 | 17.00 | 14.80 |
| | | | | | | | | | | | 37.00 | 32.20 | 28.00 | 24.40 | 21.20 | 18.40 |

VASCULAR AGE CALCULATOR (NON-LABORATORY PARAMETERS): MEN

STEP 1: CALCULATE TOTAL CVD POINTS

| CVD Points | Chronological Age (YRS) | Body Mass Index (kg/m$^2$) | Systolic BP (mmHg) Not Treated | Systolic BP (mmHg) Treated | Current Smoker | Diabetic |
|---|---|---|---|---|---|---|
| -7 | | | | | | |
| -6 | | | | | | |
| -5 | | | | | | |
| -4 | | | | | | |
| -3 | 25-29 | | | | | |
| -2 | | | <120 | | | |
| -1 | | | | | | |
| 0 | 30-34 | <25 | 120-129 | <120 | NO | NO |
| 1 | | 25-<30 | 130-139 | | | |
| 2 | 35-39 | ≥30 | 140-159 | 120-129 | | |
| 3 | | | 160+ | 130-139 | | YES |
| 4 | | | | 140-159 | YES | |
| 5 | 40-44 | | | 160+ | | |
| 6 | | | | | | |
| 7 | 45-49 | | | | | |
| 8 | 50-54 | | | | | |
| 9 | | | | | | |
| 10 | 55-59 | | | | | |
| 11 | 60-64 | | | | | |
| 12 | | | | | | |
| 13 | 65-69 | | | | | |
| 14 | 70-74 | | | | | |
| 15 | 75+ | | | | | |
| Point Subtotals: | | | | | | |

FIG. 6

STEP 2: CONVERT TOTAL CVD POINTS TO VASCULAR AGE

| TOTAL CVD POINTS FROM STEP 1 | %FMDmax ≥0 | 1 | 2 | 3 | 4 | 5 | 6 | 7 | 8 | 9 | 10 | 11 | 12 | 13 | 14 | 15+ |
|---|---|---|---|---|---|---|---|---|---|---|---|---|---|---|---|---|
| −9  | 31  | 30  | 28  | 27  | 26  | 24  | 23  | 22  | 21  | 20  | 19  | 19  | 18  | <18 | <18 | <18 |
| −8  | 32  | 31  | 30  | 29  | 27  | 26  | 25  | 24  | 23  | 22  | 21  | 20  | 19  | 18  | <18 | <18 |
| −7  | 35  | 33  | 32  | 30  | 29  | 27  | 26  | 25  | 24  | 23  | 22  | 21  | 20  | 19  | 18  | <18 |
| −6  | 37  | 35  | 33  | 32  | 31  | 29  | 28  | 27  | 25  | 24  | 23  | 22  | 21  | 20  | 19  | 18  |
| −5  | 38  | 37  | 36  | 34  | 33  | 31  | 30  | 28  | 27  | 26  | 25  | 23  | 22  | 21  | 20  | 19  |
| −4  | 41  | 39  | 37  | 35  | 34  | 32  | 31  | 30  | 28  | 27  | 26  | 24  | 23  | 22  | 21  | 20  |
| −3  | 42  | 40  | 38  | 37  | 35  | 33  | 32  | 31  | 29  | 28  | 27  | 25  | 24  | 23  | 22  | 21  |
| −2  | 44  | 42  | 40  | 38  | 37  | 35  | 33  | 32  | 30  | 29  | 28  | 27  | 25  | 24  | 23  | 22  |
| −1  | 47  | 45  | 43  | 41  | 39  | 37  | 35  | 34  | 32  | 31  | 29  | 28  | 27  | 26  | 24  | 23  |
| 0   | 50  | 47  | 45  | 43  | 41  | 39  | 38  | 36  | 34  | 33  | 31  | 30  | 28  | 27  | 26  | 24  |
| 1   | 53  | 51  | 48  | 46  | 44  | 42  | 40  | 38  | 37  | 35  | 33  | 32  | 31  | 29  | 28  | 27  |
| 2   | 56  | 54  | 51  | 49  | 47  | 45  | 42  | 41  | 39  | 37  | 35  | 34  | 32  | 31  | 29  | 28  |
| 3   | 58  | 55  | 52  | 50  | 48  | 45  | 43  | 42  | 40  | 38  | 36  | 35  | 33  | 32  | 30  | 29  |
| 4   | 62  | 58  | 55  | 52  | 50  | 48  | 46  | 44  | 41  | 40  | 38  | 36  | 34  | 33  | 32  | 31  |
| 5   | 64  | 61  | 58  | 56  | 53  | 51  | 48  | 46  | 44  | 42  | 40  | 38  | 37  | 35  | 33  | 32  |
| 6   | 68  | 65  | 62  | 59  | 56  | 54  | 51  | 49  | 46  | 45  | 43  | 41  | 39  | 37  | 35  | 33  |
| 7   | 72  | 69  | 65  | 63  | 60  | 57  | 54  | 51  | 49  | 47  | 45  | 43  | 41  | 39  | 38  | 36  |
| 8   | 73  | 70  | 66  | 63  | 61  | 58  | 55  | 52  | 50  | 48  | 46  | 44  | 42  | 40  | 39  | 37  |
| 9   | 78  | 73  | 70  | 67  | 64  | 61  | 58  | 55  | 53  | 50  | 48  | 46  | 44  | 42  | 40  | 38  |
| 10  | 80  | 78  | 74  | 70  | 68  | 64  | 61  | 58  | 56  | 54  | 51  | 49  | 47  | 45  | 43  | 40  |
| 11  | >80 | 79  | 75  | 71  | 69  | 65  | 62  | 59  | 57  | 55  | 52  | 50  | 48  | 46  | 44  | 41  |
| 12  | >80 | >80 | 79  | 75  | 72  | 68  | 65  | 63  | 60  | 57  | 54  | 52  | 50  | 48  | 46  | 44  |
| 13  | >80 | >80 | 79  | 76  | 73  | 69  | 66  | 64  | 61  | 58  | 55  | 53  | 51  | 49  | 47  | 45  |
| 14  | >80 | >80 | >80 | 79  | 77  | 73  | 70  | 66  | 64  | 61  | 58  | 56  | 54  | 51  | 49  | 47  |
| 15  | >80 | >80 | >80 | 80  | 78  | 74  | 71  | 67  | 65  | 62  | 59  | 57  | 55  | 52  | 50  | 48  |
| 16+ | >80 | >80 | >80 | >80 | >80 | 79  | 75  | 72  | 69  | 66  | 64  | 61  | 58  | 56  | 54  | 52  |

VASCULAR AGE (YEARS)

VASCULAR AGE CALCULATOR (LABORATORY PARAMETERS): MEN

STEP 1: CALCULATE TOTAL CVD POINTS

| CVD Points | Chronological Age (YRS) | HDL Cholesterol (mg/dL) | Total Cholesterol (mg/dL) | Systolic BP (mmHg) Not Treated | Systolic BP (mmHg) Treated | Current Smoker | Diabetic |
|---|---|---|---|---|---|---|---|
| -7 | | | | | | | |
| -6 | | | | | | | |
| -5 | | | | | | | |
| -4 | | | | | | | |
| -3 | 25-29 | | | | | | |
| -2 | | 60+ | | <120 | | | |
| -1 | | 50-59 | | | | | |
| 0 | 30-34 | 45-49 | <160 | 120-129 | <120 | NO | NO |
| 1 | | 35-44 | 160-199 | 130-139 | | | |
| 2 | 35-39 | <35 | 200-239 | 140-159 | 120-129 | | |
| 3 | | | 240-279 | 160+ | 130-139 | | YES |
| 4 | | | 280+ | | 140-159 | YES | |
| 5 | 40-44 | | | | 160+ | | |
| 6 | 45-49 | | | | | | |
| 7 | | | | | | | |
| 8 | 50-54 | | | | | | |
| 9 | | | | | | | |
| 10 | 55-59 | | | | | | |
| 11 | 60-64 | | | | | | |
| 12 | 65-69 | | | | | | |
| 13 | | | | | | | |
| 14 | 70-74 | | | | | | |
| 15 | 75+ | | | | | | |
| Point Subtotals: | | | | | | | |

FIG. 7

STEP 2: CONVERT TOTAL CVD POINTS TO VASCULAR AGE

| TOTAL CVD POINTS FROM STEP 1 | %FMDmax ≥0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| -11 | 26 | 24 | 23 | 22 | 21 | 20 | 19 | 18 | <18 | <18 | <18 | <18 | <18 | <18 | <18 | <18 |
| -10 | 27 | 26 | 25 | 23 | 22 | 21 | 20 | 19 | 19 | 18 | <18 | <18 | <18 | <18 | <18 | <18 |
| -9 | 28 | 27 | 26 | 25 | 24 | 23 | 22 | 21 | 20 | 19 | 18 | <18 | <18 | <18 | <18 | <18 |
| -8 | 30 | 29 | 27 | 26 | 25 | 24 | 23 | 22 | 21 | 20 | 19 | 18 | <18 | <18 | <18 | <18 |
| -7 | 32 | 31 | 29 | 28 | 27 | 25 | 24 | 23 | 22 | 21 | 20 | 19 | 18 | <18 | <18 | <18 |
| -6 | 34 | 32 | 31 | 29 | 28 | 27 | 26 | 24 | 23 | 22 | 21 | 20 | 19 | 19 | 18 | 18 |
| -5 | 36 | 35 | 33 | 31 | 30 | 28 | 27 | 26 | 25 | 24 | 23 | 22 | 21 | 20 | 19 | 19 |
| -4 | 38 | 36 | 35 | 33 | 32 | 30 | 29 | 27 | 26 | 25 | 24 | 23 | 22 | 21 | 20 | 20 |
| -3 | 40 | 38 | 37 | 35 | 33 | 32 | 30 | 29 | 27 | 26 | 25 | 24 | 23 | 22 | 21 | 21 |
| -2 | 41 | 40 | 38 | 37 | 35 | 33 | 32 | 30 | 29 | 27 | 26 | 25 | 24 | 23 | 22 | 22 |
| -1 | 43 | 42 | 40 | 38 | 36 | 34 | 33 | 31 | 30 | 29 | 27 | 26 | 25 | 24 | 23 | 23 |
| 0 | 45 | 43 | 41 | 40 | 38 | 36 | 35 | 33 | 31 | 30 | 28 | 27 | 26 | 25 | 24 | 24 |
| 1 | 48 | 46 | 44 | 42 | 40 | 38 | 36 | 35 | 33 | 32 | 30 | 29 | 27 | 26 | 25 | 25 |
| 2 | 52 | 49 | 47 | 45 | 43 | 41 | 39 | 37 | 35 | 34 | 32 | 31 | 29 | 28 | 27 | 26 |
| 3 | 55 | 53 | 50 | 48 | 46 | 44 | 42 | 40 | 38 | 36 | 34 | 33 | 31 | 30 | 29 | 27 |
| 4 | 58 | 55 | 53 | 50 | 48 | 46 | 44 | 42 | 40 | 38 | 36 | 35 | 33 | 32 | 30 | 29 |
| 5 | 59 | 56 | 54 | 51 | 49 | 47 | 45 | 43 | 41 | 39 | 37 | 36 | 34 | 33 | 31 | 30 |
| 6 | 64 | 60 | 57 | 54 | 52 | 49 | 47 | 45 | 42 | 41 | 39 | 37 | 36 | 34 | 33 | 31 |
| 7 | 66 | 63 | 60 | 57 | 55 | 52 | 50 | 48 | 45 | 43 | 41 | 40 | 38 | 36 | 35 | 33 |
| 8 | 70 | 67 | 64 | 61 | 58 | 56 | 53 | 50 | 48 | 46 | 44 | 42 | 40 | 38 | 36 | 35 |
| 9 | 72 | 68 | 65 | 62 | 59 | 57 | 54 | 51 | 49 | 47 | 45 | 43 | 41 | 39 | 37 | 36 |
| 10 | 76 | 72 | 69 | 65 | 62 | 59 | 57 | 54 | 52 | 49 | 47 | 45 | 43 | 41 | 39 | 37 |
| 11 | 80 | 76 | 72 | 69 | 66 | 63 | 59 | 57 | 55 | 52 | 50 | 48 | 46 | 45 | 43 | 41 |
| 12 | >80 | 77 | 73 | 70 | 67 | 64 | 60 | 58 | 56 | 53 | 51 | 49 | 47 | 46 | 44 | 42 |
| 13 | >80 | >80 | 77 | 74 | 70 | 67 | 64 | 61 | 58 | 56 | 53 | 51 | 49 | 47 | 45 | 43 |
| 14 | >80 | >80 | >80 | 78 | 74 | 71 | 68 | 65 | 62 | 59 | 56 | 54 | 52 | 48 | 46 | 44 |
| 15 | >80 | >80 | >80 | 78 | 75 | 72 | 69 | 66 | 63 | 60 | 57 | 55 | 53 | 49 | 47 | 45 |
| 16 | >80 | >80 | >80 | >80 | 79 | 76 | 72 | 69 | 66 | 63 | 60 | 57 | 55 | 52 | 50 | 48 |
| 17 | >80 | >80 | >80 | >80 | >80 | 77 | 73 | 70 | 67 | 64 | 61 | 58 | 56 | 53 | 51 | 49 |
| 18+ | >80 | >80 | >80 | >80 | >80 | >80 | 78 | 74 | 71 | 68 | 65 | 62 | 59 | 56 | 54 | 51 |

VASCULAR AGE (YEARS)

VASCULAR AGE CALCULATOR (NON-LABORATORY PARAMETERS): WOMEN

STEP 1: CALCULATE TOTAL CVD POINTS

| CVD Points | Chronological Age (YRS) | Body Mass Index (kg/m²) | Systolic BP (mmHg) Not Treated | Systolic BP (mmHg) Treated | Current Smoker | Diabetic |
|---|---|---|---|---|---|---|
| -7 | | | | | | |
| -6 | | | | | | |
| -5 | | | | | | |
| -4 | | | | | | |
| -3 | 25-29 | | | | | |
| -2 | | | | | | |
| -1 | | | <120 | | | |
| 0 | 30-34 | <25 | | <120 | NO | NO |
| 1 | | 25-<30 | 120-129 | | | |
| 2 | 35-39 | ≥30 | 130-139 | 120-129 | | |
| 3 | | | 140-149 | 130-139 | | |
| 4 | | | 150-159 | | YES | |
| 5 | 40-44 | | 160+ | 140-149 | | YES |
| 6 | 45-49 | | | 150-159 | | |
| 7 | | | | | | |
| 8 | 50-54 | | | 160+ | | |
| 9 | | | | | | |
| 10 | 55-59 | | | | | |
| 11 | 60-64 | | | | | |
| 12 | 65-69 | | | | | |
| 13 | | | | | | |
| 14 | 70-74 | | | | | |
| 15 | 75+ | | | | | |
| Point Subtotals: | | | | | | |

STEP 2: CONVERT TOTAL CVD POINTS TO VASCULAR AGE

%FMDmax

| TOTAL CVD POINTS FROM STEP 1 | ≤0 | 1 | 2 | 3 | 4 | 5 | 6 | 7 | 8 | 9 | 10 | 11 | 12 | 13 | 14 | 15+ |
|---|---|---|---|---|---|---|---|---|---|---|---|---|---|---|---|---|
| -10 | 31 | 29 | 27 | 26 | 25 | 24 | 22 | 21 | 20 | 19 | 18 | <18 | <18 | <18 | <18 | <18 |
| -9 | 32 | 30 | 29 | 28 | 26 | 25 | 24 | 22 | 21 | 20 | 19 | 18 | <18 | <18 | <18 | <18 |
| -8 | 33 | 32 | 31 | 29 | 28 | 26 | 25 | 24 | 23 | 21 | 20 | 19 | 18 | <18 | <18 | <18 |
| -7 | 36 | 34 | 33 | 31 | 29 | 28 | 27 | 25 | 24 | 23 | 22 | 21 | 20 | 19 | 18 | <18 |
| -6 | 38 | 36 | 34 | 33 | 31 | 30 | 28 | 27 | 25 | 24 | 23 | 22 | 21 | 20 | 19 | 18 |
| -5 | 40 | 38 | 36 | 35 | 33 | 31 | 30 | 28 | 27 | 25 | 24 | 23 | 22 | 21 | 20 | 19 |
| -4 | 42 | 40 | 38 | 36 | 35 | 33 | 31 | 30 | 28 | 27 | 25 | 24 | 23 | 22 | 21 | 20 |
| -3 | 45 | 43 | 41 | 39 | 37 | 35 | 33 | 32 | 30 | 28 | 27 | 26 | 25 | 24 | 23 | 21 |
| -2 | 46 | 44 | 42 | 40 | 38 | 36 | 34 | 32 | 31 | 29 | 28 | 27 | 26 | 25 | 24 | 22 |
| -1 | 48 | 46 | 44 | 42 | 39 | 37 | 36 | 34 | 32 | 31 | 29 | 28 | 27 | 26 | 25 | 23 |
| 0 | 52 | 49 | 47 | 44 | 42 | 40 | 38 | 36 | 34 | 32 | 31 | 29 | 28 | 27 | 26 | 24 |
| 1 | 55 | 51 | 49 | 47 | 44 | 42 | 40 | 38 | 36 | 34 | 33 | 31 | 29 | 28 | 27 | 25 |
| 2 | 58 | 55 | 52 | 50 | 47 | 45 | 43 | 40 | 38 | 36 | 35 | 33 | 31 | 30 | 28 | 27 |
| 3 | 61 | 58 | 55 | 53 | 50 | 47 | 45 | 43 | 41 | 38 | 37 | 35 | 33 | 32 | 30 | 28 |
| 4 | 65 | 62 | 59 | 56 | 53 | 50 | 48 | 46 | 43 | 41 | 39 | 37 | 35 | 34 | 32 | 30 |
| 5 | 69 | 66 | 62 | 59 | 56 | 53 | 51 | 48 | 45 | 43 | 41 | 39 | 37 | 36 | 34 | 32 |
| 6 | 70 | 66 | 63 | 60 | 57 | 54 | 52 | 49 | 46 | 44 | 42 | 40 | 38 | 37 | 35 | 33 |
| 7 | 73 | 70 | 66 | 63 | 60 | 57 | 54 | 51 | 48 | 46 | 44 | 42 | 40 | 38 | 37 | 35 |
| 8 | 78 | 74 | 70 | 67 | 64 | 60 | 57 | 54 | 51 | 49 | 47 | 45 | 42 | 40 | 38 | 36 |
| 9 | >80 | 77 | 74 | 70 | 67 | 64 | 61 | 58 | 54 | 52 | 50 | 47 | 45 | 42 | 40 | 38 |
| 10 | >80 | 78 | 75 | 71 | 68 | 65 | 61 | 58 | 55 | 53 | 51 | 48 | 46 | 43 | 41 | 39 |
| 11 | >80 | >80 | 78 | 75 | 72 | 68 | 64 | 61 | 58 | 55 | 53 | 50 | 48 | 45 | 43 | 42 |
| 12 | >80 | >80 | 79 | 76 | 73 | 69 | 65 | 62 | 59 | 56 | 54 | 51 | 49 | 46 | 44 | 43 |
| 13 | >80 | >80 | 80 | 77 | 76 | 73 | 69 | 65 | 60 | 57 | 55 | 52 | 50 | 47 | 45 | 44 |
| 14 | >80 | >80 | >80 | 80 | 77 | 74 | 70 | 66 | 61 | 59 | 56 | 53 | 51 | 48 | 46 | 45 |
| 15 | >80 | >80 | >80 | 80 | 78 | 75 | 71 | 67 | 62 | 60 | 57 | 54 | 52 | 49 | 47 | 46 |
| 16+ | >80 | >80 | >80 | >80 | 78 | 75 | 73 | 69 | 63 | 61 | 58 | 55 | 53 | 50 | 48 | 47 |

VASCULAR AGE (YEARS)

FIG. 10

VASCULAR AGE CALCULATOR (LABORATORY PARAMETERS): WOMEN

STEP 1: CALCULATE TOTAL CVD POINTS

| CVD Points | Chronological Age (YRS) | HDL Cholesterol (mg/dL) | Total Cholesterol (mg/dL) | Systolic BP (mmHg) Not Treated | Systolic BP (mmHg) Treated | Current Smoker | Diabetic |
|---|---|---|---|---|---|---|---|
| -5 | | | | | | | |
| -4 | | | | | | | |
| -3 | | | | | | | |
| -2 | | 60+ | | | | | |
| -1 | | 50-59 | | <120 | | | |
| 0 | 30-34 | 45-49 | <160 | 120-129 | | NO | NO |
| 1 | | 35-44 | 160-199 | 130-139 | | | |
| 2 | 35-39 | <35 | | 140-149 | 120-129 | | |
| 3 | | | 200-239 | | 130-139 | YES | |
| 4 | 40-44 | | 240-279 | 150-159 | 140-149 | | YES |
| 5 | 45-49 | | 280+ | 160+ | 150-159 | | |
| 6 | | | | | 160+ | | |
| 7 | 50-54 | | | | | | |
| 8 | 55-59 | | | | | | |
| 9 | 60-64 | | | | | | |
| 10 | 65-69 | | | | | | |
| 11 | 70-74 | | | | | | |
| 12 | 75+ | | | | | | |
| Point Subtotals: | | | | | | | |

FIG. 11

STEP 2: CONVERT TOTAL CVD POINTS TO VASCULAR AGE

%FMDmax

| TOTAL CVD POINTS FROM STEP 1 | ≤0 | 1 | 2 | 3 | 4 | 5 | 6 | 7 | 8 | 9 | 10 | 11 | 12 | 13 | 14 | 15+ |
|---|---|---|---|---|---|---|---|---|---|---|---|---|---|---|---|---|
| -10 | 26 | 25 | 23 | 22 | 21 | 20 | 18 | <18 | <18 | <18 | <18 | <18 | <18 | <18 | <18 | <18 |
| -9  | 29 | 27 | 25 | 24 | 22 | 21 | 20 | 19 | 18 | <18 | <18 | <18 | <18 | <18 | <18 | <18 |
| -8  | 31 | 29 | 27 | 26 | 24 | 23 | 21 | 20 | 19 | 18 | <18 | <18 | <18 | <18 | <18 | <18 |
| -7  | 34 | 31 | 29 | 27 | 26 | 24 | 23 | 21 | 20 | 19 | 18 | <18 | <18 | <18 | <18 | <18 |
| -6  | 36 | 33 | 31 | 29 | 28 | 26 | 25 | 23 | 22 | 20 | 19 | 18 | <18 | <18 | <18 | <18 |
| -5  | 38 | 36 | 34 | 31 | 30 | 28 | 26 | 25 | 23 | 22 | 20 | 19 | 18 | <18 | <18 | <18 |
| -4  | 41 | 38 | 36 | 34 | 32 | 30 | 28 | 26 | 25 | 23 | 22 | 21 | 20 | 18 | <18 | <18 |
| -3  | 43 | 41 | 39 | 36 | 34 | 32 | 30 | 28 | 27 | 25 | 24 | 22 | 21 | 20 | 18 | 19 |
| -2  | 47 | 44 | 42 | 39 | 37 | 35 | 32 | 31 | 29 | 27 | 25 | 24 | 22 | 21 | 20 | 20 |
| -1  | 49 | 46 | 43 | 41 | 38 | 36 | 34 | 32 | 30 | 28 | 27 | 25 | 23 | 22 | 21 | 21 |
| 0   | 50 | 47 | 44 | 42 | 39 | 37 | 35 | 33 | 31 | 29 | 28 | 26 | 24 | 23 | 22 | 22 |
| 1   | 55 | 52 | 49 | 46 | 43 | 41 | 38 | 36 | 34 | 31 | 30 | 28 | 26 | 25 | 23 | 23 |
| 2   | 58 | 55 | 51 | 49 | 46 | 43 | 40 | 38 | 36 | 34 | 31 | 30 | 28 | 26 | 25 | 25 |
| 3   | 62 | 59 | 55 | 52 | 49 | 46 | 43 | 41 | 38 | 36 | 34 | 32 | 30 | 28 | 26 | 28 |
| 4   | 68 | 64 | 60 | 56 | 53 | 50 | 47 | 44 | 41 | 39 | 37 | 34 | 32 | 30 | 29 | 29 |
| 5   | 73 | 68 | 64 | 60 | 57 | 53 | 50 | 47 | 45 | 42 | 39 | 37 | 35 | 33 | 31 | 30 |
| 6   | 74 | 69 | 65 | 61 | 58 | 54 | 51 | 48 | 45 | 43 | 40 | 38 | 36 | 34 | 32 | 31 |
| 7   | 79 | 75 | 70 | 65 | 62 | 58 | 55 | 51 | 48 | 45 | 43 | 40 | 38 | 36 | 34 | 34 |
| 8   | >80 | 80 | 75 | 70 | 66 | 62 | 58 | 55 | 51 | 49 | 46 | 43 | 40 | 38 | 36 | 36 |
| 9   | >80 | >80 | 80 | 75 | 71 | 65 | 62 | 58 | 55 | 52 | 49 | 46 | 43 | 41 | 38 | 37 |
| 10  | >80 | >80 | >80 | 76 | 72 | 66 | 63 | 59 | 56 | 53 | 50 | 47 | 44 | 42 | 39 | 38 |
| 11  | >80 | >80 | >80 | 75 | 71 | 67 | 64 | 60 | 57 | 54 | 51 | 48 | 45 | 43 | 41 | 39 |
| 12  | >80 | >80 | >80 | 78 | 74 | 68 | 65 | 61 | 58 | 55 | 52 | 49 | 46 | 44 | 42 | 41 |
| 13  | >80 | >80 | >80 | >80 | 78 | 73 | 69 | 65 | 60 | 57 | 54 | 51 | 48 | 45 | 43 | 42 |
| 14  | >80 | >80 | >80 | >80 | 79 | 74 | 70 | 66 | 61 | 58 | 55 | 52 | 49 | 46 | 44 | 43 |
| 15+ | >80 | >80 | >80 | >80 | 80 | 75 | 70 | 67 | 62 | 59 | 56 | 53 | 50 | 47 | 45 | 43 |

VASCULAR AGE (YEARS)

FIG. 12

SYSTEM AND METHOD FOR USING FLOW-MEDIATED DILATION TO PROVIDE AN ADJUSTED VASCULAR AGE AS AN INDICATOR OF RISK OF CARDIOVASCULAR DISEASE

CROSS REFERENCE TO RELATED APPLICATION

This application claims the benefit of U.S. provisional application No. 61/778,424, filed 13 Mar. 2013, which is hereby incorporated by reference as though fully set forth herein.

BACKGROUND a. Field

The present disclosure relates generally to assessing a person's risk of developing cardiovascular disease. In particular, the present disclosure relates to a vascular age calculator based on flow-mediated dilation.

b. Background

Cardiovascular disease (CVD) is a leading cause of morbidity and mortality. Consequently, CVD risk assessment continues to be a key focus in primary medical care settings.

Multivariable risk prediction algorithms have been used to assess CVD risk and guide treatment of risk factors. For example, the Framingham Heart Study (FHS), based on a long-term study of a population of individuals, relates age, total and high-density lipoprotein cholesterol, systolic blood pressure, treatment for hypertension, smoking, and diabetes status to a quantitative risk of CVD, expressed as a percent chance of having a CVD event in ten years. General CVD risk point scores and vascular age data are described in D'Agostino et al., "General Cardiovascular Risk Profile for Use in Primary Care: The Framingham Heart Study," *Circulation* 2008, 117:743-753.

More recent CVD risk assessment techniques have focused on the correlation between early stage CVD and the ability of arteries to dilate in response to increased blood flow. Brachial artery flow-mediated dilation (FMD) has been used by numerous investigators to evaluate cardiovascular health. One study, Inaba et al., "Prediction of future Cardiovascular Outcomes by Flow-Mediated Vasodilation of Brachial Artery: A Meta-Analysis," *Int J Cardiovasc Imaging* 2010, 26:631-640, determined a pooled relative risk (0.87) of cardiovascular events per 1% increase in brachial artery FMD.

U.S. Pat. No. 8,057,400, which is commonly owned and incorporated herein by reference in its entirety, describes a medical diagnostic method, device, and system for non-invasively assessing the ability of arteries to respond to an increase in blood flow. Volume pulse wave amplitudes or other components are used to provide an indication of FMD, and, consequently, CVD risk.

SUMMARY

A diagnostic tool and method are used to modify vascular age scoring systems using flow-mediated dilation (FMD) data. The resulting FMD-adjusted vascular age calculator can be used to diagnose a person's potential for developing cardiovascular disease.

A method of diagnosing a person's potential for developing (CVD) in accordance with one embodiment of the present teachings includes the following steps: a) determining a first best-fit equation for preexisting data assigning original CVD points to a plurality of physiological parameters, wherein said plurality of physiological parameters include chronological ages; b) extrapolate using the first best-fit equation to assign extrapolated CVD points to younger and older chronological ages than said chronological ages in said preexisting data; c) using said original CVD points and said extrapolated CVD points to determine a lowest total CVD points possible and a highest total CVD points possible for said physiological parameters; d) determining a second best-fit equation for said preexisting data assigning CVD risk data to total CVD points; e) extrapolate using the second best-fit equation to assign extrapolated CVD risk data to a plurality of total CVD points ranging from said lowest total CVD points possible to said highest total CVD points possible; f) assigning said extrapolated CVD risk data to a selected percent flow-mediated dilation (% FMD) value selected from a plurality of % FMD values, wherein said plurality of % FMD values includes values above and below said selected % FMD value; g) expanding said extrapolated CVD risk data to account for said plurality of % FMD values, thereby creating expanded CVD risk data; h) using the second best-fit equation to assign total CVD points to each value in said expanded CVD risk data, thereby creating a plurality of assigned total CVD points; i) determining a third best-fit equation for said preexisting data assigning vascular ages to CVD risk data; j) using the third best-fit equation and said plurality of assigned total CVD points to calculate vascular ages corresponding to each value in said expanded CVD risk data; k) determining a fourth best-fit equation assigning said vascular ages to adjusted selected % FMDmax values; l) reassigning said vascular ages to said plurality of % FMD values based on said adjusted selected % FMDmax values; m) creating a vascular age calculator comprising a table of vascular ages corresponding to said plurality of total CVD points and said plurality of FMD values; and n) using said vascular age calculator to diagnose the person's potential for developing cardiovascular disease.

A method of diagnosing a person's potential for developing CVD in accordance with another embodiment of the present teachings includes the following steps: a) determining a relative post-occlusion change in a vessel diameter of an artery in an extremity via reactive hyperemia; b) calculating a vascular age using at least said determined change in said vessel diameter and a parameter indicative of flow-mediated dilation (FMD) in said vessel; and c) presenting said calculated vascular age.

A diagnostic tool in accordance with one embodiment of the present teachings includes the following: a) a first storage operable to store first data relating to a patient's general risk of developing cardiovascular disease based upon a plurality of physiological parameters; b) a device operable to determine a parameter indicative of FMD in a limb arterial blood vessel; and c) a processor in communication with said first storage and in communication with said device, wherein said processor is operable to do the following: (1) apply said parameter to said stored first data to convert said general risk for developing cardiovascular disease to a vascular age; and (2) output said vascular age.

A system for providing real-time vascular age information to a patient in accordance with one embodiment of the present teachings includes a diagnostic tool comprising the following: a) a first storage operable to store first data relating to a patient's general risk of developing cardiovascular disease based upon a plurality of physiological parameters; b) a device operable to determine a parameter indicative of FMD in a limb arterial blood vessel; and c) a processor in communication with said first storage and in communication with said device, wherein said processor is operable to do the following: (1) apply said parameter to said stored first data to convert said general risk for developing cardiovascular disease to a vascular age; and (2) output said vascular age; a communication network linked to said diagnostic tool; and a mobile device linked to said communication network, the mobile device configured to display said vascular age.

BRIEF DESCRIPTION OF THE DRAWINGS

FIG. 4 is a table displaying exemplary extrapolated CVD risk data adjusted for % FMDmax.

FIG. 5 is a table for calculating total CVD points for men with non-laboratory parameters in accordance with an embodiment of the present disclosure.

FIG. 6 is a table for converting total CVD points to vascular age for men with non-laboratory parameters in accordance with an embodiment of the present disclosure.

FIG. 7 is a table for calculating total CVD points for men with laboratory parameters in accordance with an embodiment of the present disclosure.

FIG. 8 is a table for converting total CVD points to vascular age for men with laboratory parameters in accordance with an embodiment of the present disclosure.

FIG. 9 is a table for calculating total CVD points for women with non-laboratory parameters in accordance with an embodiment of the present disclosure.

FIG. 10 is a table for converting total CVD points to vascular age for women with non-laboratory parameters in accordance with an embodiment of the present disclosure.

FIG. 11 is a table for calculating total CVD points for women with laboratory parameters in accordance with an embodiment of the present disclosure.

FIG. 12 is a table for converting total CVD points to vascular age for women with laboratory parameters in accordance with an embodiment of the present disclosure.

DETAILED DESCRIPTION

Figure 1:
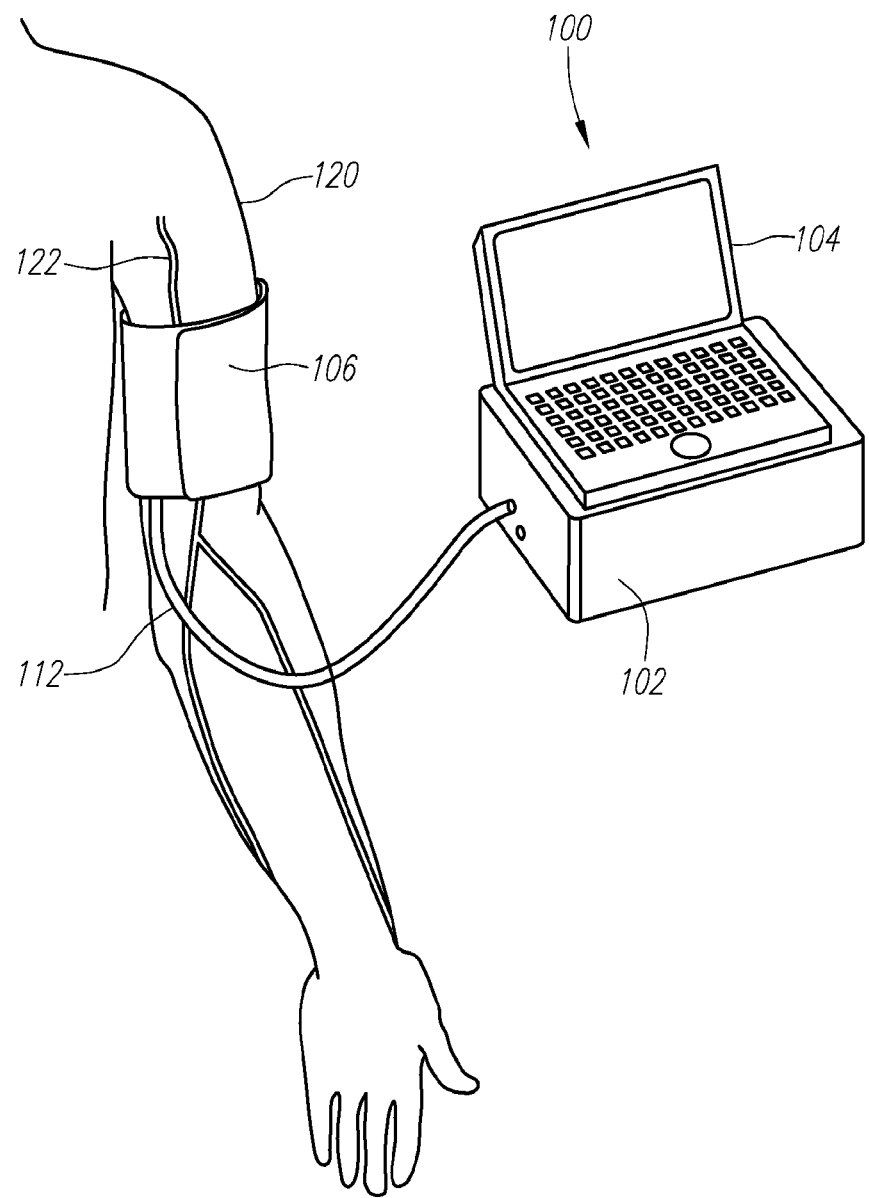
FIG. 1 is a pictorial diagram illustrating a diagnostic system accordance with an embodiment of the present invention.

Referring now to the drawings, wherein like reference numerals are used to identify identical components in the various views, FIG. 1 is a pictorial diagram illustrating a diagnostic system 100 for calculating a subject's vascular age or health age (also referred to as "wellness age" or "physiological age"). Vascular age can be defined as the equivalent age of a person with the same calculated cardiovascular risk but whose risk factors are all within normal ranges. For example, a 50-year-old man with high cardiovascular risk factors (e.g., increased blood pressure, overweight, smoker, etc.), could have a vascular age of 60. The diagnostic system 100 illustrated in FIG. 1 may include a diagnostic device 102, a diagnostic computer 104, and a cuff 106.

As used herein, volume pulse waves are oscillations in blood pressure between the systolic and the diastolic pressures of arteries. The diagnostic system 100 can detect the volume pulse waves and perform diagnostics for assessing arterial volume changes of a limb segment based on the detected pulse waves. In some embodiments, the volume pulse wave can include a composite pulse wave formed of a superposition of a plurality of component pulse waves. The component pulse waves can partially overlap and the arterial pulse wave shape or contour can be formed by the superposition of the component pulse waves. The component pulse waves can include, for example, an incident systolic wave (also called early systolic wave), a reflected wave (also called late systolic wave), and other waves. The diagnostic system 100 can measure amplitudes of components of arterial volume pulse waves as a way of monitoring the changes in arterial volume of the limb segment after a stimulus. While it may be easier to measure the amplitude of the whole arterial volume pulse wave, the timing of the component pulse waves shifts throughout the testing procedure and changes the shape of the pulse wave. In some embodiments, the diagnostic system 100 can measure the amplitude of a physiologically significant component (such as a component pulse wave) of the volume pulse wave to assess the changes in arterial volume of the limb segment. The diagnostic system 100 can use any component pulse wave of the detected volume pulse wave or portion thereof (such as maximum, inflection point, or amplitude at a fixed time of the component pulse wave), any portion of the volume pulse wave (such as maximum, inflection point, or amplitude at a fixed time of the volume pulse wave), or a combination thereof for the diagnostics for assessing arterial volume changes. As an illustrative example, the operation of the diagnostic system 100 is described herein in terms of the early systolic wave.

In use, the cuff 106 can be disposed around a limb 120 so that when the cuff 106 is inflated, the cuff 106 constricts a segment of the limb 120. It is understood by those skilled in the art that the measurements of the changes in the arterial volume of a limb segment described herein are not measuring the volume changes of only a single artery in the limb 120, but are measuring the volume changes in substantially all arteries in the segment of the limb 120 that is being constricted. Although the volume change measurements and the physiology thereof are described for a single artery, one skilled in the art will recognize that the invention is not restricted to a single artery and that the volume changes measurements are of all or substantially all arteries in the segment of the limb being measured. The limb 120 may be any limb or digits thereof, but for the sake of simplicity, the limb 120 is described as an arm, and the artery that is being evaluated is described as the brachial artery. In some embodiments, the limb 120 is a leg and the artery is a femoral artery. Although the diagnostic system 100 is described for use on a human being, the invention is not so limited. The diagnostic system 100 can be used on other mammals.

The diagnostic computer 104 can provide control signals to the diagnostic device 102 and receive information and detected data from the diagnostic device 102.

The diagnostic device 102 can provide air to and release air from the cuff 106 via a tube 112 of the cuff 106. The diagnostic device 102 can control, detect, and monitor the air pressure in the tube 112. In some embodiments, a gas other than air, or a liquid, such as water, may be used in the cuff 106 and the tube 112. In some embodiments, the cuff 106 can be an electrically-controlled elastomer or a mechanically-controlled material.

Although the diagnostic system 100 is described herein as applying a pressure via the cuff 106 to the limb 120 to occlude an artery 122 as a stimulus of the endothelium prompting vasodilation as blood flows into the artery 122 after release of the occlusion, other forms of stimuli may be provided. In various embodiments, the stimulus of the endothelium comprises a mechanical stimulation, a thermal stimulation, a chemical stimulation, an electrical stimulation, a neurological stimulation, a mental stimulation or a stimulation via physical exercise, or any combination thereof, to induce a change in arterial volume of the limb segment. Some stimuli may induce formation of nitric oxide by the endothelial cells lining the walls of the arteries. In some embodiments, the stimulus to the endothelium can also be delivered in any way that transiently and locally increases the blood flow and shear stress at the arterial wall. For instance, this can be achieved by applying ultrasound waves such that it creates turbulence inside a major artery. The chemical stimulation may be, for example, a vasoactive agent, such as an intra-brachial infusion of acetylcholine.

Although the diagnostic computer 104 is described herein as performing the control, computation, and analysis of the diagnostic system 100, the invention is not so limited. The diagnostic device 102 can include a processor or microcontroller for performing any or all of the operations described herein as being performed by the diagnostic computer 104.

Although the diagnostic computer 104 is described herein as being local to the blood diagnostic device 102, the diagnostic computer 104 can be coupled to the diagnostic device 102 through a communication line, system, or network, such as the Internet, wireless, or landline. For example, the operation of the diagnostic device 102 can be done near the patient while the diagnostic computer 104 can remotely process the data.

Figure 2:
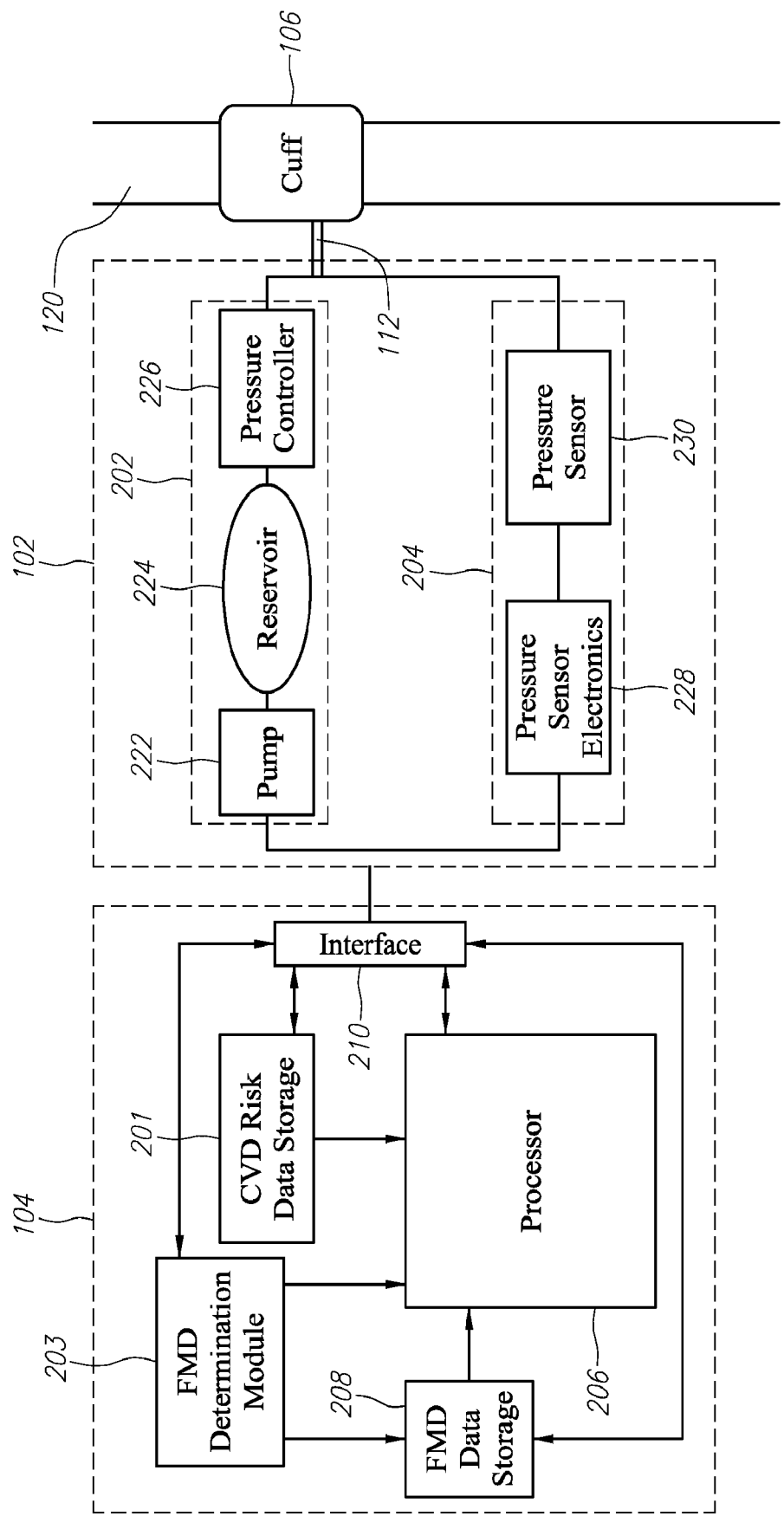
FIG. 2 is a block diagram illustrating the diagnostic system of FIG. 1.

FIG. 2 is a block diagram illustrating further details of the diagnostic device 102 and the diagnostic computer 104. The diagnostic device 102 comprises a pneumatic module 202 and a pressure detector 204. The pneumatic module 202 can control pressure in the cuff 106 in response to control signals from the diagnostic computer 104. The pneumatic module 202 comprises a pump 222 (e.g., an air pump) for pressurizing air, a reservoir 224 for storing the pressurized air, and a pressure controller 226 for controlling the release of air via the tube 112, into the cuff 106.

The pressure detector 204 comprises a pressure sensor electronics system 228 for controlling a pressure sensor 230, which can sense pressure in the cuff 106 via the tube 112. The pressure sensor 230 can detect pressure oscillations in the cuff 106 resulting from pulse waves in the artery 122. In some embodiments, the pressure sensor 230 can be disposed in the cuff 106 or in the tube 112. In some embodiments, the pressure sensor 230 can be a plethysmography sensor, such as a reflective photo-plethysmography sensor or a pneumoplethysmography sensor.

The diagnostic computer 104 comprises a cardiovascular disease (CVD) risk data storage 201, a flow-mediated dilation (FMD) determination module 203, a processor 206, a FMD data storage 208, and an interface 210. The CVD risk storage 201 can be configured to store a patient's CVD risk data. In an example, CVD risk data can include Framingham Heart Study (FHS) multi-year risk scores, European Systemic Coronary Risk Evaluation (SCORE) values, or other clinicopathologic input data, including chronological age, gender, body mass index, systolic blood pressure, resting heart rate, breath flow analysis, smoking status, presence or absence of diabetes, blood glucose level and/or hemoglobin A1c, HDL cholesterol, total cholesterol, other lipid measures, carotid artery intima-media wall thickness (CIMT) detected via ultrasound, pulse wave velocity/amplitude waveform analysis, brachial artery ultrasound imaging, fingertip temperature analysis, pedometer data, sleep patterns, stress levels, blood-based biomarkers, genomic data, and other metrics related to longevity. Patient-specific CVD risk data can be entered directly into diagnostic computer 104 and stored in CVD risk storage 201. Alternatively, CVD risk data can be accessed via a network or cloud-based communication channel linked to processor 206 or interface 210.

The FMD determination module 203 can be configured to determine a parameter indicative of a patient's FMD in a limb arterial blood vessel, such as the brachial artery. Parameters indicative of a patient's FMD can include maximum percent arterial dilation post-occlusion compared with pre-occlusion (% FMDmax), time (e.g., from cuff release following occlusion) to % FMDmax, 60-second FMD, or 90-second FMD, for example. % FMDmax can be determined from the maximum percent change in blood volume post-occlusion vs. pre-occlusion, which, in turn, can be determined from the maximum percent change in blood pressure post-occlusion vs. pre-occlusion, as measured by cuff 106 and reflected as pulse wave amplitude changes by pressure sensor 230 (described above with respect to FIG. 1). In other embodiments, % FMDmax can also be determined via other means. For example, % FMDmax can be determined by using a pneumoplethysmograph without sensors or via vascular ultrasonography by using an ultrasound imager.

The FMD data storage 208 can be configured to store parameters indicative of a patient's FMD. This data can be received from the FMD determination module 203 or from another source via a network or cloud-based communication channel linked to processor 206 or interface 210.

The processor 206 can be communicatively linked to the CVD risk data storage 201, the FMD determination module 203, and the FMD data storage 208. The processor can be configured to apply a parameter indicative of a patient's FMD to the stored CVD risk data, thereby converting the CVD risk data to a vascular age or health age. The process for converting CVD risk data to vascular age is described below with respect to FIG. 3. The processor 206 can be configured to perform mathematical calculations using a licensed downloaded copy of MedCalc® Version 13.0.0.0 (http://www.medcalc.org) or a similar software program. The processor 206 can further be configured to output vascular age data via a user interface display of diagnostic computer 104 or another device linked via a network or cloud-based communication channel to processor 206.

The interface 210 can communicate control signals and information signals between the diagnostic computer 104 and the pneumatic module 202, the pressure detector 204, the CVD risk data storage 201, the FMD determination module 203, the processor 206, and the FMD data storage 208. The interface 210 can include an additional processor or microcontroller for performing any or all of the operations described herein.

Figure 13:
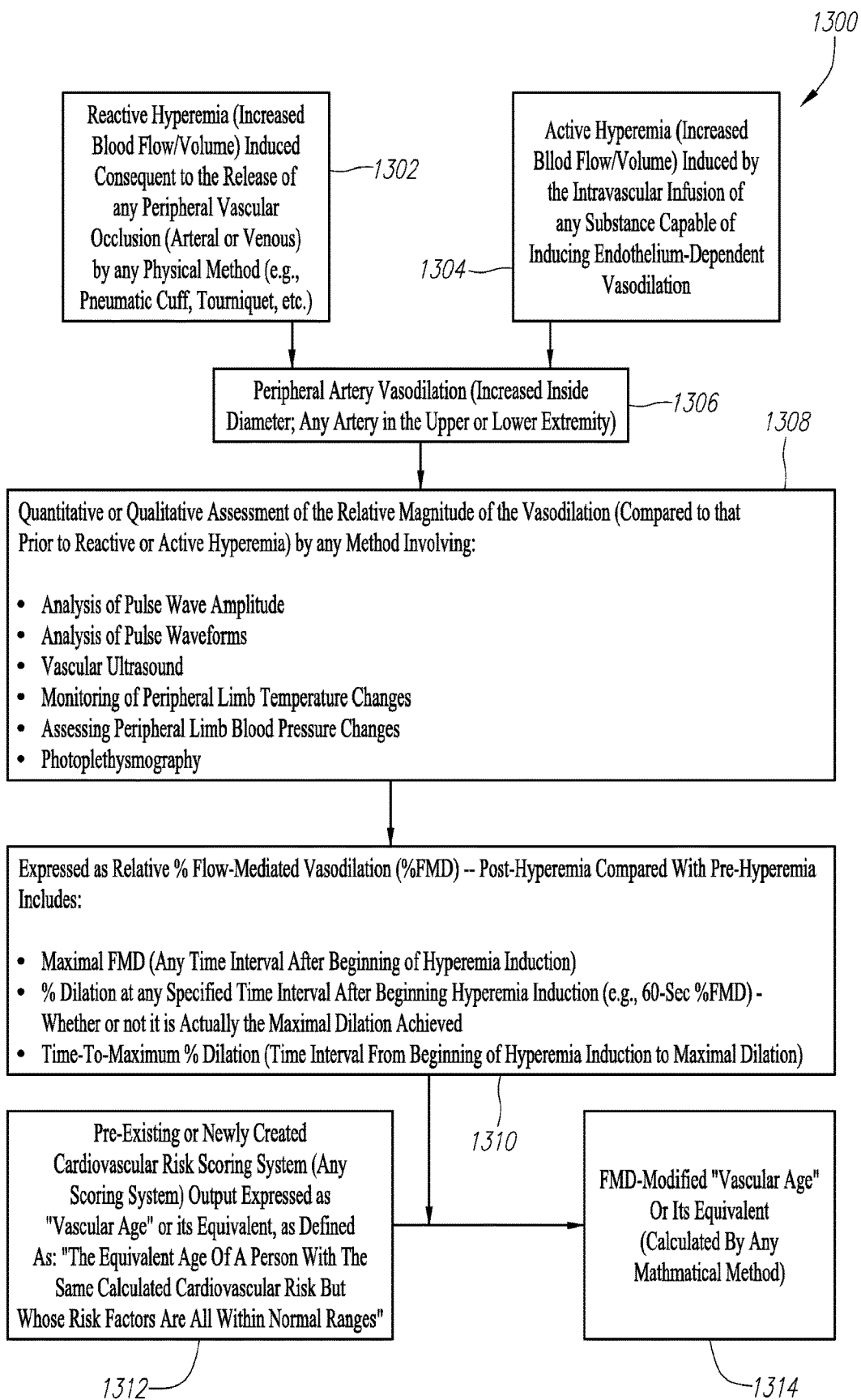
FIG. 13 is a flow chart illustrating an overview of a method for calculating a FMD-modified vascular age in accordance with an embodiment of the present disclosure.
Figure 14:
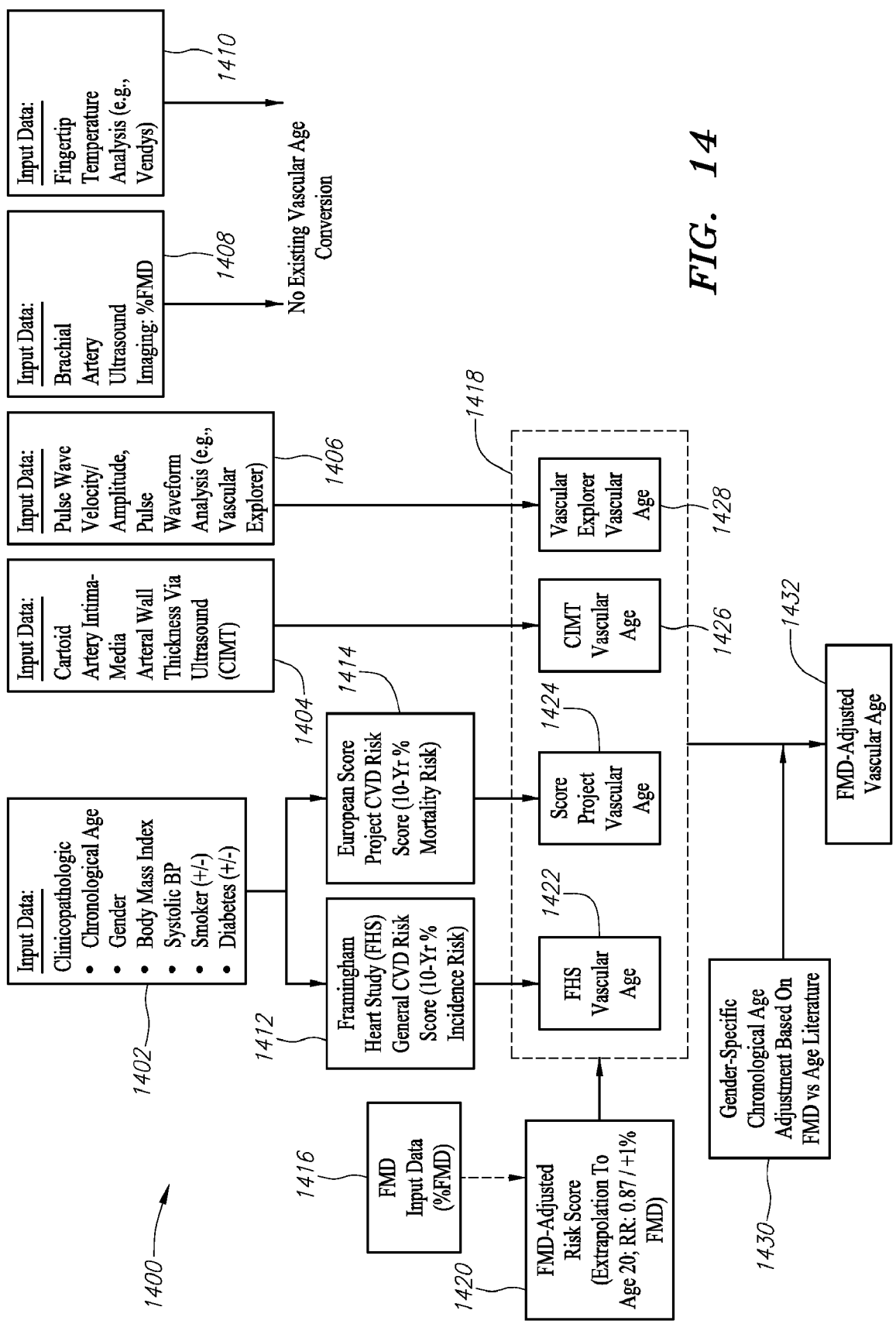
FIG. 14 is a flow chart illustrating an overview of various methods for calculating FMD-adjusted vascular age by adjusting preexisting measures of vascular age in accordance with an embodiment of the present disclosure.

FIGS. 13 and 14 are flow charts providing general overviews of methods for calculating vascular age. It may be helpful to the reader review these high-level flow charts prior to continuing with the description of the detailed method for calculating vascular age described below with respect to FIG. 3. FIG. 13 is a flow chart illustrating an overview of a method 1300 for calculating a FMD-modified vascular age. At 1302 and 1304, either reactive or active hyperemia is induced in a subject. Reactive hyperemia can be induced consequent to the release of any peripheral vascular (arterial or venous) occlusion by any physical means, such as by cuff 106 (see FIGS. 1 and 2). Active hyperemia can be induced by the intravascular infusion of any substance capable of inducing endothelium-dependent vasodilation, such as those described above with respect to FIG. 1 and in U.S. Pat. No. 8,057,400. Once reactive or active hyperemia has been induced, peripheral artery vasodilation can occur at 1306. Quantitative or qualitative assessment of the relative magnitude of this vasodilation (compared to that prior to reactive or active hyperemia) can occur at 1308. This assessment can be done via any method, including, but not limited to, analysis of pulse wave amplitudes (e.g., as detected by pressure sensor 230 in FIG. 2), analysis of pulse waveforms, vascular ultrasound, monitoring of peripheral limb temperature changes, or assessment of peripheral limb blood pressure changes. At 1310, the assessment of the relative magnitude of vasodilation can be expressed as a relative percent flow-mediated dilation (% FMD). FMD can be defined as the vasodilatory response of a vessel to elevations in blood flow-associated shear stress. Vasoactive substances (e.g., nitric oxide) are released by endothelial cells in response to shear stress, which leads to FMD. Healthy people typically have a higher % FMD than patients with endothelial dysfunction. FMD can be measured at 1310 as the maximal FMD detected at any time interval after hyperemia induction, the percent dilation at any specified time interval after hyperemia induction (e.g., 60-second % FMD), or the time it takes to reach % FMDmax from the start of hyperemia induction. At 1312, vascular age values obtained from pre-existing or newly created CVD scoring systems (e.g. Framingham Heart Study or European SCORE project) can be modified by the FMD data measured at step 1310 to produce FMD-modified vascular age values. An exemplary method for calculating FMD-modified vascular age is described below with respect to FIG. 3.

FIG. 14 is a flow chart illustrating an overview of various methods 1400 for calculating an FMD-adjusted vascular age by adjusting preexisting measures of vascular age. At 1402, various clinicopathologic data—including chronological age, gender, body mass index, systolic blood pressure, smoking status, and diabetes status—are used to determine a FHS CVD risk score at 1412 or a European SCORE project CVD risk score at 1414. The FHS CVD risk score can be used to calculate a FHS vascular age at 1422, and the European SCORE project CVD risk score can be used to calculate a SCORE project vascular age at 1424. Any of the results of existing vascular age calculators (see box 1418) can be modified using FMD data at 1416 and 1420, as well as gender specific chronological age FMD data at 1430, to determine an FMD-adjusted vascular age at 1432. The FMD data used to modify results of any of the existing vascular age calculators can be determined by any method, including, but not limited to, analysis of pulse wave amplitude (e.g., such as performed by AngioDefender™ of Everist Health, Inc., EndoPAT of Itamar Medical, Ltd., or Vascular Explorer of Enverdis® GmbH); analysis of pulse wave forms (e.g., such as performed by AngioDefender™ or Vascular Explorer, or as described in PCT pat. appl. WO 2011/016712), vascular ultrasound (e.g., generic brachial artery ultrasound imaging or generic carotid intima media thickness ultrasound imaging); monitoring of peripheral limb temperature changes; assessing peripheral limb blood pressure changes; or photoplethysmography.

Input data other than that listed at 1402 can be used to calculate vascular age. For example, at 1404, carotid artery intima-media arterial wall thickness (CIMT) measured via ultrasound can be used to calculate a CIMT vascular age at 1426. Similarly, at 1406, pulse wave velocity/amplitude waveform analysis (e.g., as performed by Vascular Explorer) can be used to calculate a Vascular Explorer vascular age at 1428. These vascular age measurements can be modified using FMD data at 1416 and 1420, as well as gender specific chronological age FMD data at 1430, to determine a FMD-adjusted vascular age at 1432. For other forms of input data, such as % FMD determined by brachial artery ultrasound imaging at 1408 or fingertip temperature analysis (e.g., as performed by Vendys® of Endothelix, Inc.) at 1410, there is no existing vascular age conversion. Nevertheless, future vascular age calculators could be developed using these (or other) data and subsequently modified using FMD data at 1416 and 1420, as well as gender specific chronological age FMD data at 1430, to determine an FMD-adjusted vascular age at 1432. Again, the FMD data used to modify results of any of the existing or future vascular age calculators can be determined by any method, including as those listed above.

Figure 3:
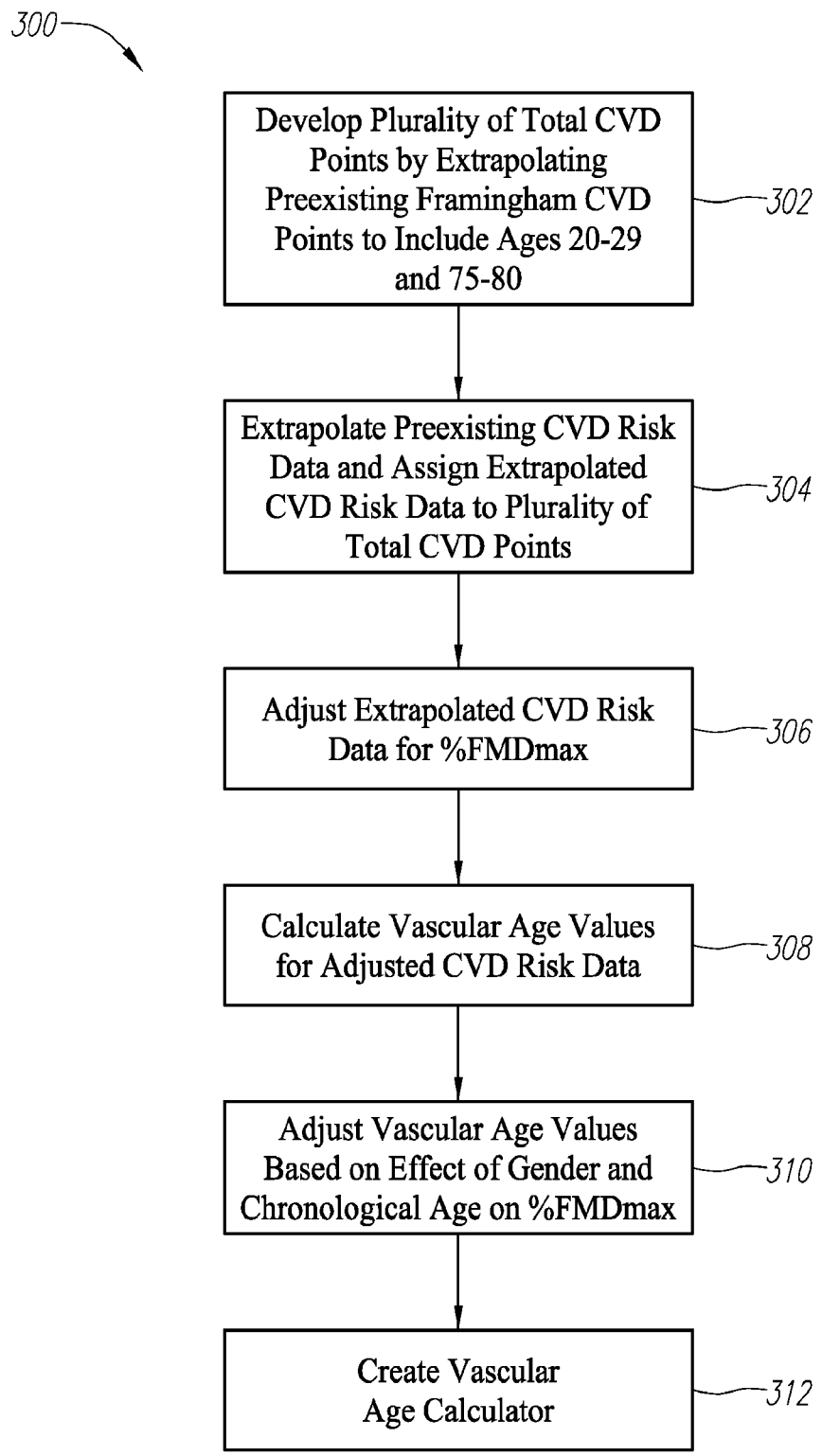
FIG. 3 is a flow chart illustrating an example of a method for creating a vascular age calculator in accordance with an embodiment the present invention.

Referring now to FIG. 3, a method 300 for creating a vascular age or health age calculator according to the present disclosure is shown. The method 300 can be used in conjunction with diagnostic system 100, for example. In particular, the method 300 can be performed by the processor 206. At step 302, Framingham CVD points can be extrapolated to include ages 20-29 and 75-80. A best-fit logarithmic regression equation can be used to perform this extrapolation. Step 302 can be performed separately for different demographic populations and for different input data sets. For example, Framingham CVD points can be assigned differently according to gender, chronological age, and the specific physiological parameters used to determine the CVD points. Physiological parameters can include, for example, non-laboratory parameters alone or both non-laboratory and laboratory parameters. Non-laboratory parameters can include body mass index (kg/m$^2$), treated or untreated systolic blood pressure (mmHg), smoking status, and presence or absence of diabetes, for example. Laboratory parameters can include HDL cholesterol (mg/dL) and total cholesterol (mg/dL), for example. Thus, four separate best-fit equations can be developed—one for men with no labs, one for men with labs, one for women with no labs, and one for women with labs. (As used herein, "with no labs" or "with non-laboratory parameters" indicates only non-laboratory parameters are being used, and "with labs" or "with laboratory parameters" indicates that both laboratory and one or more non-laboratory parameters are being used.) In each case, the best-fit equation can be Log(Y)=a+bX, where X=CVD points, Y=chronological age, and a and b are calculated numerical values based on the preexisting Framingham data for each demographic population. The best-fit equations developed by the present inventors for extrapolating CVD risk points to include ages 20-29 are as follows:

$$\text{Log}(Y)=1.5080+0.02492X \text{ for men with no labs;} \quad (1)$$

$$\text{Log}(Y)=1.5097+0.02542X \text{ for men with labs;} \quad (2)$$

$$\text{Log}(Y)=1.5097+0.02542X \text{ for women with no labs; and} \quad (3)$$

$$\text{Log}(Y)=1.5027+0.03200X \text{ for women with labs.} \quad (4)$$

Equations (1)-(4) can vary, however, based on the specific physiological parameters that taken into account. Using these equations, CVD points can be extrapolated and assigned to ages 20-29. The extrapolated CVD points for ages 20-29, together with the preexisting Framingham CVD points for ages 30-75, can be used to determine the lowest and highest total CVD points possible for a given set of physiological parameters. In the above examples, the lowest possible total CVD points was determined to be −9 for men with no labs, −11 for men with labs, and −10 for women with and without labs. In another embodiment, extrapolated CVD points for ages 75-80 can also be taken into account when determining the lowest and highest total CVD points possible for a given set of physiological parameters.

At step 304, a second extrapolation can be performed after determining a second best-fit equation for preexisting Framingham data by assigning CVD risk score (e.g., a percentage) to CVD point values. This second best-fit equation can then be extrapolated to assign extrapolated CVD risk scores to a plurality of total CVD points ranging from the lowest CVD points possible to the highest CVD points possible. Again, separate second best-fit equations can be developed for men with no labs, men with labs, women with no labs, women with labs. In each case, the second best-fit equation can be Log(Y)=a+bX, where X=CVD points, Y=CVD risk (%), and a and b are calculated numerical values based on the preexisting Framingham data for each demographic population. The second best-fit equations developed by the present inventors for extrapolating CVD risk scores are as follows:

$$\text{Log}(Y)=0.3651+0.07521X \text{ for men with no labs;} \quad (5)$$

$$\text{Log}(Y)=0.2140+0.07507X \text{ for men with labs;} \quad (6)$$

$$\text{Log}(Y)=0.1057+0.06811X \text{ for women with no labs; and} \quad (7)$$

$$\text{Log}(Y)=0.09715+0.06898X \text{ for women with labs.} \quad (8)$$

Equations (5)-(8) can vary, however, based on the specific physiological parameters that are taken into account.

At step 306, the extrapolated CVD risk scores can be adjusted to take into account a flow-mediated dilation measurement (e.g., % FMDmax). This adjustment can be accomplished by first assigning extrapolated CVD risk scores to a selected % FMDmax value (e.g. a median or mean % FMDmax value) selected from a plurality of % FMDmax values, including values above and below the selected % FMDmax value. In an example, the selected % FMDmax value can be between about 4% and about 18%, or, more specifically, about 10% based on the results of several published population-based studies (see, e.g., Shechter et al., "Long-Term Association of Brachial Artery Flow-Mediated Dilation and Cardiovascular Events in Middle-Aged Subjects with No Apparent Heart Disease," Int J Cardiol 2009, 134:52-58; Yeboah et al., "Predictive Value of Brachial Flow-Mediated Dilation for Incident Cardiovascular Events in a Population-Based Study: The Multi-Ethnic Study of Atherosclerosis," Circulation 2009, 120:502-509; and Wierzbicka-Chmiel et al., "The Relationship Between Cardiovascular Risk Estimated by Use of SCORE System and Intima Media Thickness and Flow Mediated Dilation in a Low Risk Population," Cardiol J 2009, 16:407-412). Next, the extrapolated CVD risk scores can be expanded to account for the plurality of % FMDmax values, thereby creating expanded FMD-adjusted CVD risk scores. The expansion of CVD risk scores can be accomplished by multiplying Framingham CVD risk score values by a relative risk factor between about 0.85 and 0.95 (see, e.g. Ras et al., "Flow-Mediated Dilation and Cardiovascular Risk Prediction: A Systemic Review with Meta-Analysis," Int J Cardiol 2012, http://dx.dot.org/10.1016/j.ijcard.2012.09.047). Using a relative risk factor of 0.87 based on Inaba et al., referenced above, Framingham CVD risk score values can be multiplied by [1/0.87] for % FMDmax values less than 10 (e.g., between 0 and 9) and by 0.87 for % FMDmax values greater than 10 (e.g., between 11 and 15+). Finally, one of equations (5)-(8) can be used to assign total CVD points to each value in the expanded CVD risk scores, thereby creating a plurality of assigned total CVD points.

Exemplary results of step 306 can be seen in FIG. 4, a table displaying extrapolated CVD risk scores adjusted for % FMDmax for men with no labs. In column 402, total CVD points are listed in ascending order from −9 to 16+. In row 404, % FMDmax is listed in ascending order from 0 to 15+. Column 428 corresponds to a % FMDmax value of 10. This is the selected % FMDmax value to which extrapolated CVD risk scores are assigned. Column 426, corresponding to a % FMDmax value of 9, can then be populated with FMD-adjusted CVD risk scores by multiplying the CVD risk score values in each row of column 428 by [1/0.87]. For example, in row 440, corresponding to a total CVD point value of −9, 0.48 is the CVD risk score value corresponding to a % FMDmax of 10. 0.48 is multiplied by [1/0.87] to get 0.55, the CVD risk score value corresponding to a % FMDmax of 9. Then, 0.55 is multiplied by [1/0.087] to get 0.63, CVD risk score value corresponding to a % FMDmax of 8. The remainder of CVD risk score values for columns 408-426 are calculated in a similar fashion. For % FMDmax values between 11 and 15+, 0.87 is the multiplication factor used to calculate CVD risk score values. This is because greater % FMDmax values (greater than 10 in this example) correlate with decreased CVD risk, Whereas lesser % FMDmax values (less than 10 in this example) correlate with higher CVD risk. Row 406 lists the CVD risk adjustment factors for each column corresponding to a % FMDmax value. For example, in column 424, corresponding to 8% FMDmax, the CVD risk adjustment factor is 1.32. Thus, 1.32 multiplied by 0.48 (CVD risk score corresponding to % FMDmax of 10) is 0.63 (CVD risk score corresponding to % FMDmax of 8). The above described calculations used to create the table displayed in FIG. 4 can be programmed to be carried out by processor 206, for example.

Returning to FIG. 3, at step 308, vascular age values can be calculated for adjusted CVD risk scores. This can be accomplished by determining a third best-fit equation for preexisting Framingham CVD points assigning vascular ages to CVD risk scores. The third best-fit equation can then be used, along with the plurality of assigned CVD points, to calculate FMD-adjusted vascular ages corresponding to each value in the FMD-adjusted expanded CVD risk scores. Again, separate third best-fit equations can be developed for men with no labs, men with labs, women with no labs, women with labs. In each case, the third best-fit equation can be Log(Y)=a+bX, where X FMD-adjusted vascular age, Y=CVD risk score (%), and a and b are calculated numerical values based on the preexisting Framingham data for each demographic population. The third best-fit equations developed by the present inventors for extrapolating CVD risk scores are as follows:

$$\text{Log}(Y)=-4.1868+3.0047 \text{ Log}(X) \text{ for men with no labs;} \quad (9)$$

$$\text{Log}(Y)=-4.1939+2.9825 \text{ Log}(X) \text{ for men with labs;} \quad (10)$$

Log($Y$)=−4.0016+2.7251 Log($X$) for women with no labs; and        (11)

Log($Y$)=−3.2177+2.2629 Log($X$) for women with labs.        (12)

Equations (9)-(12) can vary, however, based on the specific physiological parameters that taken are into account.

In step 310, the FMD-adjusted vascular age values calculated in step 308 can be used to adjust the selected % FMDmax value based on gender and chronological age. Older people are expected to have lower % FMDmax values. Similarly, % FMDmax values are expected to vary based on gender. To correct for these variables, the following set of fourth best-fit equations have been determined by the present inventors, in which X=FMD-adjusted vascular age and Y=adjusted selected % FMDmax value:

$Y$=11.60+−0.080$X$ for men with or without labs, ages 20-45;        (13)

$Y$=13.0+−0.111$X$ for men with or without labs, ages 45-80;        (14)

$Y$=11.25+−0.0625$X$ for women with or without labs, ages 20-52;        (15)

$Y$=16.6667+−0.1667$X$ for women with or without labs, ages 52-80.        (16)

Equations (13)-(16) were developed based on the following references: Celermajer et al. "Aging is associated with endothelial dysfunction in healthy men years before the age-related decline in women," *J Am Coll Cardiol* 1994, 24:471-476; Corretti et al., "The effects of age and gender on brachial artery endothelium-dependent vasoactivity are stimulus-dependent," *Clin Cardiol* 1995, 18:471-476; Benjamin et al., "Clinical correlates and heritability of flow-mediated dilation in the community: The Framingham Heart Study," *Circulation* 2004, 109:613-619; and Skaug et al., "Age and gender differences of endothelial function in 4739 healthy adults: the HUNT3 Fitness Study," *Eur J Prevent Cardiol* 2013, 20(4):531-540. The FMD-adjusted vascular age values can then be reassigned to corresponding % FMDmax values based on the adjusted selected % FMDmax values calculated in step 310.

In step 312, a vascular age calculator can be created for each demographic population. The vascular age calculator can comprise a table, or set of tables, of vascular ages corresponding to the plurality of total CVD points and the plurality of % FMD values. In an example, a first table can be used to calculate total CVD points and a second table can be used to convert the total CVD points into a corresponding vascular age. Vascular age can be measured in years, months, days, hours, minutes, or seconds, for example. The vascular age calculator can be used to diagnose a person's potential for developing cardiovascular disease.

The method of calculating vascular age described above with respect to FIG. 3 can be consolidated into a two-step process (for each demographic population) using the tables shown in FIGS. 5-12, which were created in accordance with the above-described method. FIG. 5 is a table that can be used to calculate total CVD points for men using non-laboratory parameters. The table in FIG. 5 displays Framingham CVD points for ages 30-75 and extrapolated CVD points for ages 20-29. Each non-laboratory parameter (chronological age, body mass index, treated or untreated systolic blood pressure, smoking status, and diabetic status) is associated with a specific number of CVD points. CVD points accrued for each parameter can be added to obtain a person's total CVD points. For example, a 35-year-old non-smoking, non-diabetic man with a body mass index of 26 kg/m², and a treated systolic blood pressure of 150 mmHg would have 7 total CVD points.

Once a person's total CVD point value has been calculated using the table in FIG. 5, the total CVD point value can be converted to vascular age using the table displayed in FIG. 6 (applicable to men with non-laboratory parameters). Continuing with the example described above, a 35-year-old man with 7 total CVD points and 10% FMDmax would have a vascular age of 45. In addition to providing specific vascular age values, the table in FIG. 6 can be used to provide CVD risk categories based on FMD-adjusted vascular age. For example, the region of the table labeled 602 can be identified as low CVD risk according to FMD-adjusted vascular age, the region labeled 604 can be identified as intermediate CVD risk according to FMD-adjusted vascular age, and the region labeled 606 can be identified as high CVD risk according to FMD-adjusted vascular age.

FIGS. 7 and 8 are tables created according to method 300 for men with laboratory parameters, and they can be used to calculate vascular age in a similar two-step process to that described above with respect to FIGS. 5 and 6. In the table displayed in FIG. 8, region 802 can be identified as low CVD risk according to FMD-adjusted vascular age, the region labeled 804 can be identified as intermediate CVD risk according to FM D-adjusted vascular age, and the region labeled 806 can be identified as high CVD risk according to FMD-adjusted vascular age.

FIGS. 9 and 10 are tables created according to method 300 for women with non-laboratory parameters, and they can be used to calculate vascular age in a similar two-step process to that described above with respect to FIGS. 5 and 6. In the table displayed in FIG. 10, region 1002 can be identified as low CVD risk according to FMD-adjusted vascular age, the region labeled 1004 can be identified as intermediate CVD risk according to FMD-adjusted vascular age, and the region labeled 1006 can be identified as high CVD risk according to FMD-adjusted vascular age.

FIGS. 11 and 12 are tables created according to method 300 for women with laboratory parameters, and they can be used to calculate vascular age in a similar two-step process to that described above with respect to FIGS. 5 and 6. In the table displayed in FIG. 12, region 1202 can be identified as low CVD risk according to FMD-adjusted vascular age, the region labeled 1204 can be identified as intermediate CVD risk according to FMD-adjusted vascular age, and the region labeled 1206 can be identified as high CVD risk according to FMD-adjusted vascular age.

Figure 15:
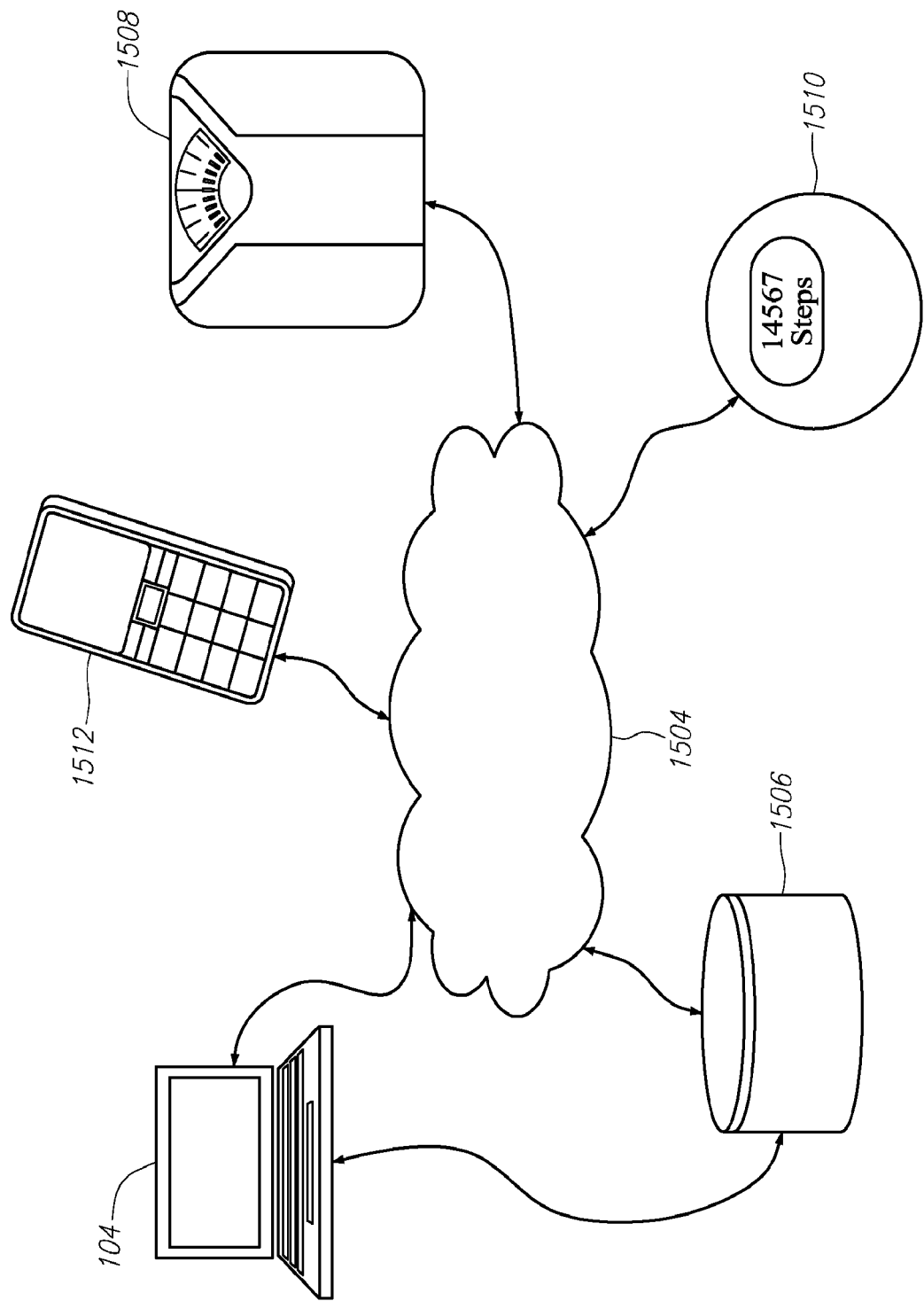
FIG. 15 is a pictorial diagram illustrating an example of a system for providing real-time vascular age information to an interested party (e.g., a patient or a physician).

FIG. 15 is a pictorial diagram illustrating an example of a system 1500 for providing real-time vascular age information to a patient. Diagnostic computer 104, described above with respect to FIG. 1, can be linked to a communication channel 1504 (e.g., a global communication network) and to a data storage 1506. The data storage 1506, which can also be linked to the communication channel 1504, can be used to store patient-specific data, such as total CVD points, CVD risk data, FMD data, % FMD-adjusted CVD risk data, and vascular age, for example. Furthermore, diagnostic devices such as a scale 1508 or a pedometer 1510, for example, can be linked, such as via communication channel 1504, to diagnostic computer 104 and/or storage 1506. CVD risk data measured by the scale 1508 and/or pedometer 1510 can be updated regularly or continuously and used by diagnostic computer 104 to update a person's calculated vascular age. In other embodiments, CVD risk data can be measured by other devices, such as a glucose meter (not shown), for example. CVD risk data can also be accessed by diagnostic computer 104 via communication channel 1504 from other sources, such as a doctor's office or hospital, for example.

A mobile device 1512, linked to communication channel 1504, can include a mobile application ("app") for storing and updating CVD risk data, as well as for calculating vascular age in conjunction with, in addition to, or instead of diagnostic computer 104. In this way, the mobile app on mobile device 1512 can be used to provide real-time updates of a person's vascular age based on regularly or continuously updated CVD risk data. In addition, the mobile app can allow a user to track his or her CVD risk data and vascular age over time, so as to measure progress towards health goals and to assess the efficacy of various interventions. The mobile app can further be configured to provide alerts to a user, such as when the user's calculated vascular age goes up or down, or when the user meets certain health goals (e.g., reaching a specified number of steps in one day or lowering his/her weight or blood pressure).

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

Although the various embodiments of the devices have been described herein in connection with certain disclosed embodiments, many modifications and variations to those embodiments may be implemented. For example, particular features, structures, or characteristics described above may be combined in any suitable manner in one or more embodiments. Thus, the particular features, structures, or characteristics illustrated or described in connection with one embodiment may be combined, in whole or in part, with the features structures, or characteristics of one or more other embodiments without limitation unless illogical or nonfunctional. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A diagnostic tool configured to diagnose a person's potential for developing cardiovascular disease (CVD), the diagnostic tool comprising the following:
   a. a first storage operable to store first data relating to a patient's general risk of developing cardiovascular disease based upon a plurality of physiological parameters;
   b. a device operable to determine, from a limb arterial blood vessel, a parameter indicative of flow-mediated dilation (FMD);
   c. a processor in communication with said first storage and in communication with said device;
   d. a second storage operable to store second data relating to the parameter indicative of FMD; wherein said processor is electrically connected to said first storage and to said second storage, said processor being adapted to adjust said first data using said second data to determine a vascular age;
   wherein said processor is operable to do the following steps:
   determining a first best-fit equation for preexisting data assigning original CVD points to a plurality of physiological parameters, wherein said plurality of physiological parameters include chronological ages;
   extrapolate using the first best-fit equation to assign extrapolated CVD points to younger and older chronological ages than said chronological ages in said preexisting data;
   determining a lowest total CVD points possible and a highest total CVD points possible for said physiological parameters based on said original CVD points and said extrapolated CVD points;
   determining a second best-fit equation for said preexisting data assigning CVD risk data to total CVD points;
   extrapolate using the second best-fit equation to assign extrapolated CVD risk data to a plurality of total CVD points ranging from said lowest total CVD points possible to said highest total CVD points possible;
   assigning said extrapolated CVD risk data to a selected percent flow-mediated dilation (% FMD) value selected from a plurality of % FMD values, wherein said plurality of % FMD values includes values above and below said selected % FMD value;
   expanding said extrapolated CVD risk data to account for said plurality of % FMD values, thereby creating expanded CVD risk data;
   assigning total CVD points to each value in said expanded CVD risk data, thereby creating a plurality of assigned total CVD points, based on the second best-fit equation;
   determining a third best-fit equation for said preexisting data assigning vascular ages to CVD risk data;
   calculating vascular ages corresponding to each value in said expanded CVD risk data based on the third best-fit equation and said plurality of assigned total CVD points;
   determining a fourth best-fit equation assigning said vascular ages to adjusted selected % FMDmax values;
   reassigning said vascular ages to said plurality of % FMD values based on said adjusted selected % FMDmax values;

creating a vascular age calculator comprising a table of vascular ages corresponding to said plurality of total CVD points and said plurality of % FMD values; and diagnosing the person's potential for developing cardiovascular disease based on the vascular age calculator.

2. The diagnostic tool of claim 1, wherein said preexisting data comprises Framingham Heart Study data.

3. The diagnostic tool of claim 1, wherein said selected % FMD value is between about 4% and about 18%.

4. The diagnostic tool of claim 3, wherein the selected % FMD value is about 10%.

5. The diagnostic tool of claim 1, wherein expanding said extrapolated CVD risk data to account for said plurality of % FMD values comprises multiplying or dividing said extrapolated CVD risk data by a relative risk factor between about 0.85 and about 0.95.

6. The diagnostic tool of claim 5, wherein the relative risk factor is 0.87.

7. The diagnostic tool of claim 1, wherein said younger chronological ages comprise ages 20-29 years; and wherein said older chronological ages comprise ages 75-80.

8. The diagnostic tool of claim 1, wherein said plurality of physiological parameters further comprises at least one of gender, body mass index, systolic blood pressure, resting heart rate, breath flow analysis, smoking status, presence or absence of diabetes, blood glucose level, hemoglobin A1c, HDL cholesterol, total cholesterol, other lipid measures, carotid artery intima-media wall thickness (CIMT) detected via ultrasound, pulse wave velocity/amplitude waveform analysis, brachial artery ultrasound imaging, fingertip temperature analysis, pedometer data, sleep patterns, stress levels, blood-based biomarkers, and genomic data.

9. The diagnostic tool of claim 1, wherein said vascular ages are calculable in years, months, weeks, days, hours, minutes, or seconds.

10. The diagnostic tool of claim 1, wherein said processor further provides for the following steps:
determining a relative post-occlusion change in a diameter of the limb arterial blood vessel via reactive hyperemia;
calculating a vascular age using at least said determined change in said diameter and a parameter indicative of flow-mediated dilation (FMD) in said vessel; and
presenting said calculated vascular age.

11. The diagnostic tool of claim 10, wherein said determining step further comprises using pneumoplethysmography.

12. The diagnostic tool of claim 10, wherein said determining step comprises temporarily occluding blood flow to said artery in said extremity.

13. The diagnostic tool of claim 10, wherein said determining step comprises temporarily creating downstream hemodynamic stress in a limb arterial blood supply, thereby inducing flow-mediated dilation.

14. The diagnostic tool of claim 10, wherein said determining step further comprises use of ultrasound images.

15. The diagnostic tool of claim 10, wherein said parameter indicative of FMD includes at least one of % FMDmax, time to % FMDmax, and X-second FMD, where X is a non-zero number.

16. The diagnostic tool of claim 1, wherein said first data is derived from data relating to said general risk of developing cardiovascular disease in a study population.

17. The diagnostic tool of claim 1, wherein said first data is derived from either FHS data or European SCORE data.

18. The diagnostic tool of claim 1, wherein said processor further provides for inputting patient-specific data selected from the group consisting of chronological age, gender, body mass index, systolic blood pressure, resting heart rat' breath flow analysis, smoking status, presence or absence of diabetes, blood glucose level, hemoglobin A1c, HDL, cholesterol, total cholesterol, other lipid measures, carotid artery intima-media wall thickness (CIMT) detected via ultrasound, pulse wave velocity/amplitude waveform analysis, brachial artery ultrasound imaging, fingertip temperature analysis, pedometer data, sleep patterns, stress levels, blood-based biomarkers, and genomic data.

19. The diagnostic tool of claim 1, wherein said device comprises a component selected from the group consisting of a pressure plethysmograph, a photoplethysmograph, and an ultrasound imager.

20. The diagnostic tool of claim 19, wherein said device comprises a pneumoplethysmograph without sensors.

21. The diagnostic tool of claim 1, wherein the parameter indicative of FMD includes at least one of % FMDmax, time to maximum % FMD, and X-second FMD, where X is a non-zero number.

22. A system for providing real-time vascular age information to a patient comprising:
a diagnostic tool configured to diagnose a person's potential for developing cardiovascular disease (CVD), the diagnostic tool comprising the following:
a first storage operable to store first data relating to a patient's general risk of developing cardiovascular disease based upon a plurality of physiological parameters;
a device operable to determine, from a limb arterial blood vessel, a parameter indicative of flow-mediated dilation (FMD);
a processor in communication with said first storage and in communication with said device;
a second storage operable to store second data relating to the parameter indicative of FMD; wherein said processor is electrically connected to said first storage and to said second storage, said processor being adapted to adjust said first data using said second data to determine a vascular age;
wherein said processor is operable to do the following steps:
determining a first best-fit equation for preexisting data assigning original CVD points to a plurality of physiological parameters, wherein said plurality of physiological parameters include chronological ages;
extrapolate using the first best-fit equation to assign extrapolated CVD points to younger and older chronological ages than said chronological ages in said preexisting data;
determining a lowest total CVD points possible and a highest total CVD points possible for said physiological parameters based on said original CVD points and said extrapolated CVD points;
determining a second best-fit equation for said preexisting data assigning CVD risk data to total CVD points;
extrapolate using the second best-fit equation to assign extrapolated CVD risk data to a plurality of total CVD points ranging from said lowest total CVD points possible to said highest total CVD points possible;
assigning said extrapolated CVD risk data to a selected percent flow-mediated dilation (% FMD) value selected from a plurality of % FMD values, wherein said plurality of % FMD values includes values above and below said selected % FMD value;

expanding said extrapolated CVD risk data to account for said plurality of % FMD values, thereby creating expanded CVD risk data;

assigning total CVD points to each value in said expanded CVD risk data, thereby creating a plurality of assigned total CVD points, based on the second best-fit equation;

determining a third best-fit equation for said preexisting data assigning vascular ages to CVD risk data;

calculating vascular ages corresponding to each value in said expanded CVD risk data based on the third best-fit equation and said plurality of assigned total CVD points;

determining a fourth best-fit equation assigning said vascular ages to adjusted selected % FMDmax values:

reassigning said vascular ages to said plurality of % FMD values based on said adjusted selected % FMDmax values;

creating a vascular age calculator comprising a table of vascular ages corresponding to said plurality of total CVD points and said plurality of % FMD values; and diagnosing the person's potential for developing cardiovascular disease based on the vascular age calculator;

a communication network linked to said diagnostic tool; and a mobile device linked to said communication network, the mobile device configured to display said vascular age.

* * * * *